(12) United States Patent
Chao et al.

(10) Patent No.: US 12,042,610 B2
(45) Date of Patent: Jul. 23, 2024

(54) ARTERIAL SHEATH WHICH ALLOWS DISTAL PERFUSION WITHIN A CANNULATED VESSEL

(71) Applicants: Tar Toong Victor Chao, Singapore (SG); Chong Hee Lim, Singapore (SG); Hock Heng Daniel Tan, Singapore (SG); Tze Kiat Ng, Singapore (SG)

(72) Inventors: Tar Toong Victor Chao, Singapore (SG); Chong Hee Lim, Singapore (SG); Hock Heng Daniel Tan, Singapore (SG); Tze Kiat Ng, Singapore (SG)

( * ) Notice: Subject to any disclaimer, the term of this patent is extended or adjusted under 35 U.S.C. 154(b) by 1351 days.

(21) Appl. No.: 16/418,729

(22) Filed: May 21, 2019

(65) Prior Publication Data
US 2019/0269888 A1 Sep. 5, 2019

Related U.S. Application Data

(63) Continuation of application No. 15/114,976, filed as application No. PCT/SG2015/050011 on Jan. 30, 2015, now abandoned.

(30) Foreign Application Priority Data
Jan. 30, 2014 (SG) ................. 2014008528

(51) Int. Cl.
*A61M 25/04* (2006.01)
*A61F 2/07* (2013.01)
(Continued)

(52) U.S. Cl.
CPC ............ *A61M 25/04* (2013.01); *A61F 2/07* (2013.01); *A61F 2/9661* (2020.05);
(Continued)

(58) Field of Classification Search
CPC .. A61M 25/04; A61M 60/104; A61M 60/178; A61M 60/196; A61M 60/857;
(Continued)

(56) References Cited

U.S. PATENT DOCUMENTS 5,178,611 A * 1/1993 Rosenberg ........ A61M 25/0017
604/172
5,330,433 A 7/1994 Fonger et al.
(Continued)

FOREIGN PATENT DOCUMENTS

WO WO-2015116003 A1 * 8/2015 .......... A61M 1/3659

*Primary Examiner* — Rebecca E Eisenberg
*Assistant Examiner* — Kate Elizabeth Strachan

(57) ABSTRACT

Defining proximal as toward the heart and distal as away from the heart, a sheath includes a proximal opening and multiple fenestrations maintainable in position slightly beyond a site or point of sheath entry into a vessel by way of an anchoring assembly having a set of radially displaceable anchoring elements configured for abutting a superficial vessel wall. The fenestrations and/or anchoring element(s) are arranged obliquely or non-obliquely around peripheral portions of the sheath. The sheath can receive blood from a pumping source at a proximal opening, and channel the blood toward, to, and through the fenestrations. The fenestrations, in combination with the proximal opening, enable the perfusion of blood into the cannulated vessel in a set of distal directions for perfusing a distal tissue or organ. Flow of blood out of fenestrations directs blood distally towards the limb, head, or other distal region, mitigating the risk of or preventing ischemia.

12 Claims, 22 Drawing Sheets

(51) Int. Cl.
*A61F 2/966* (2013.01)
*A61M 25/00* (2006.01)
*A61M 25/10* (2013.01)
*A61M 60/104* (2021.01)
*A61M 60/148* (2021.01)
*A61M 60/178* (2021.01)
*A61M 60/196* (2021.01)
*A61M 60/857* (2021.01)

(52) U.S. Cl.
CPC ...... *A61M 25/007* (2013.01); *A61M 25/0075* (2013.01); *A61M 25/0097* (2013.01); *A61M 60/104* (2021.01); *A61M 60/178* (2021.01); *A61M 60/196* (2021.01); *A61M 60/857* (2021.01); *A61M 2025/0031* (2013.01); *A61M 2025/1095* (2013.01); *A61M 60/148* (2021.01)

(58) Field of Classification Search
CPC ............ A61M 25/007; A61M 25/0097; A61M 25/0075; A61M 60/148; A61M 2025/0031; A61M 2025/1095; A61F 2/9661; A61F 2/07
See application file for complete search history.

(56) References Cited

U.S. PATENT DOCUMENTS

| | | | |
|---|---|---|---|
| 5,542,936 | A * | 8/1996 | Razi ................. A61M 25/0043 604/158 |
| 5,843,027 | A | 12/1998 | Stone et al. |
| 6,099,506 | A | 8/2000 | Macoviak et al. |
| 6,179,813 | B1 | 1/2001 | Ballow et al. |
| 6,494,909 | B2 | 12/2002 | Greenhalgh |
| 6,652,567 | B1 | 11/2003 | Deaton |
| 6,702,782 | B2 | 3/2004 | Miller et al. |
| 6,958,076 | B2 * | 10/2005 | Acosta ................. A61F 2/2412 623/2.12 |
| 8,585,679 | B2 | 11/2013 | Obrigkeit |
| 8,795,253 | B2 | 8/2014 | Moshinsky et al. |
| 8,840,636 | B2 * | 9/2014 | Barbut .......................... 606/191 |
| 10,456,518 | B2 | 10/2019 | Chao et al. |
| 2009/0259290 | A1 * | 10/2009 | Bruszewski ............. A61F 2/07 623/1.13 |

* cited by examiner

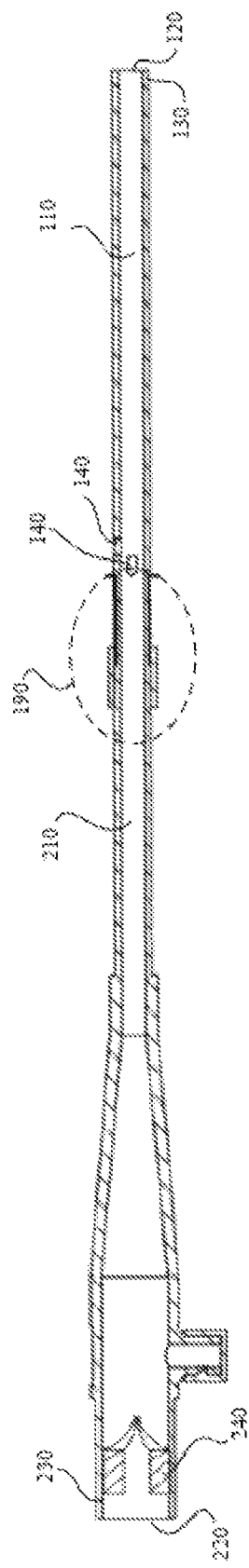
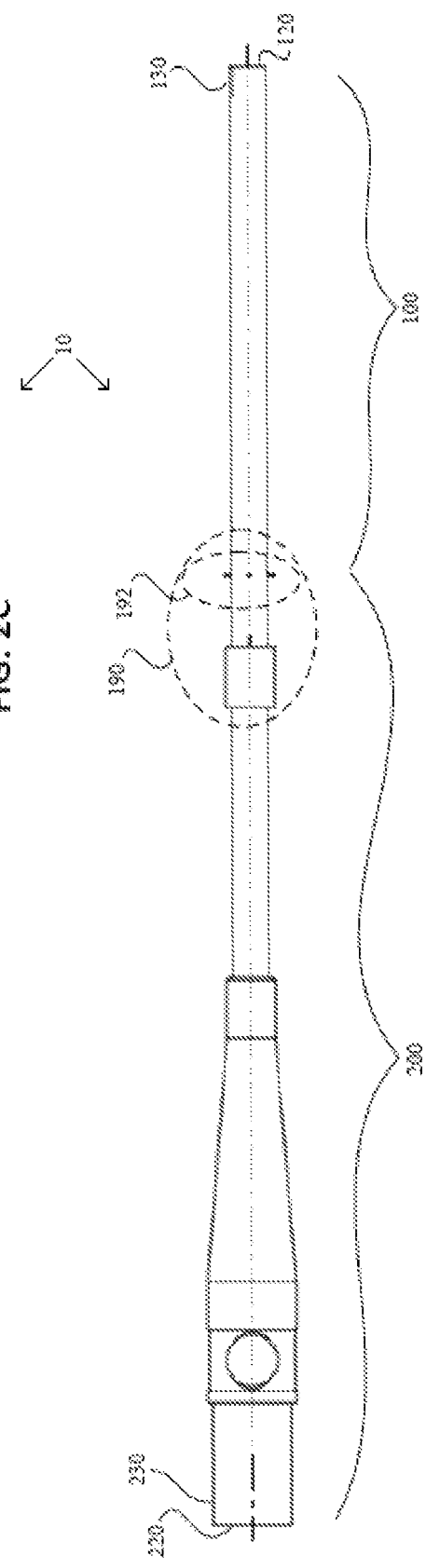
FIG. 2C
FIG. 2D

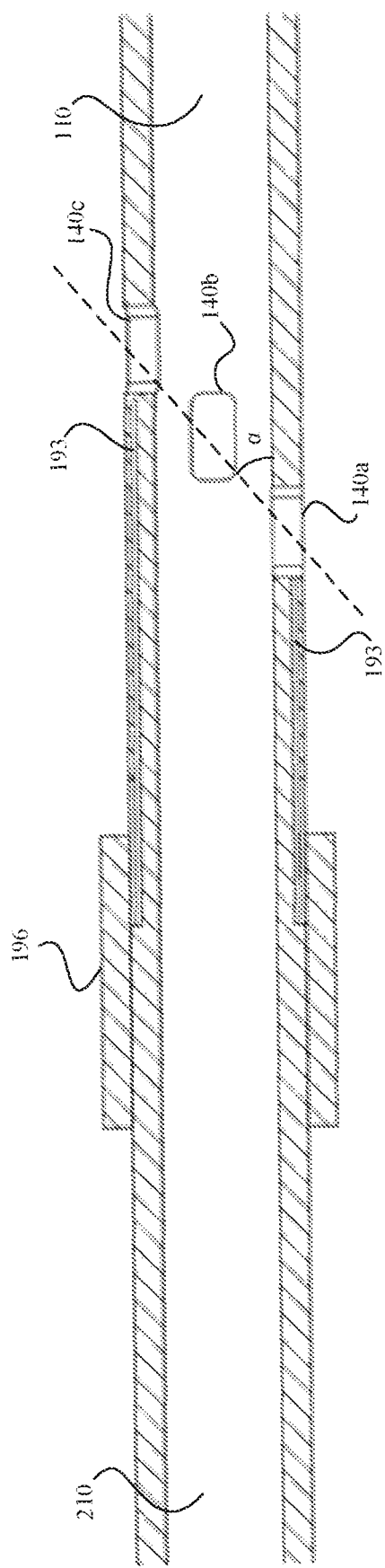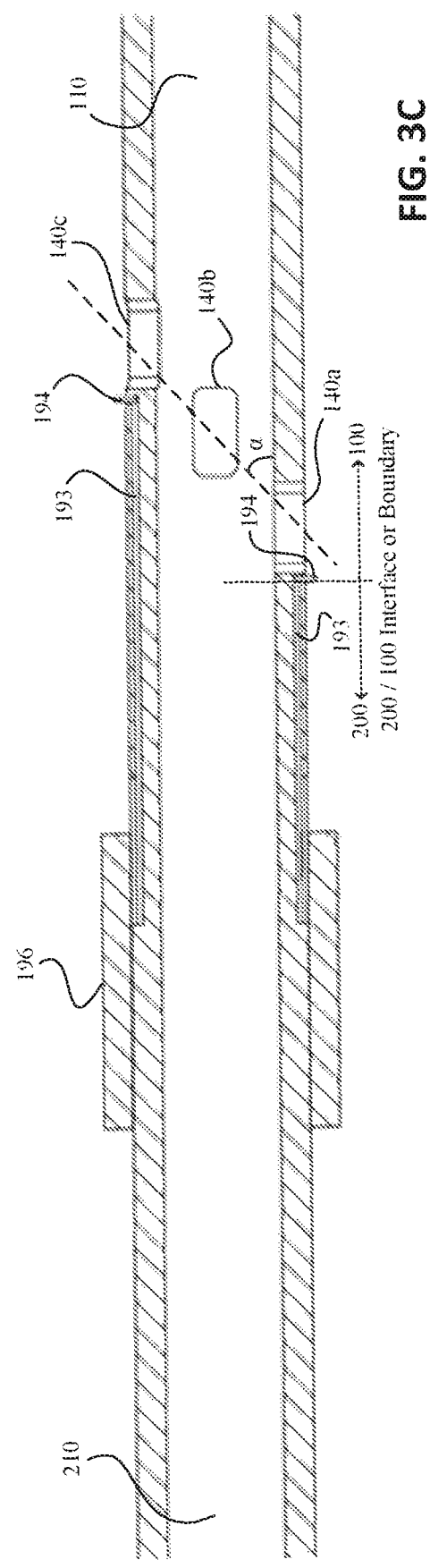

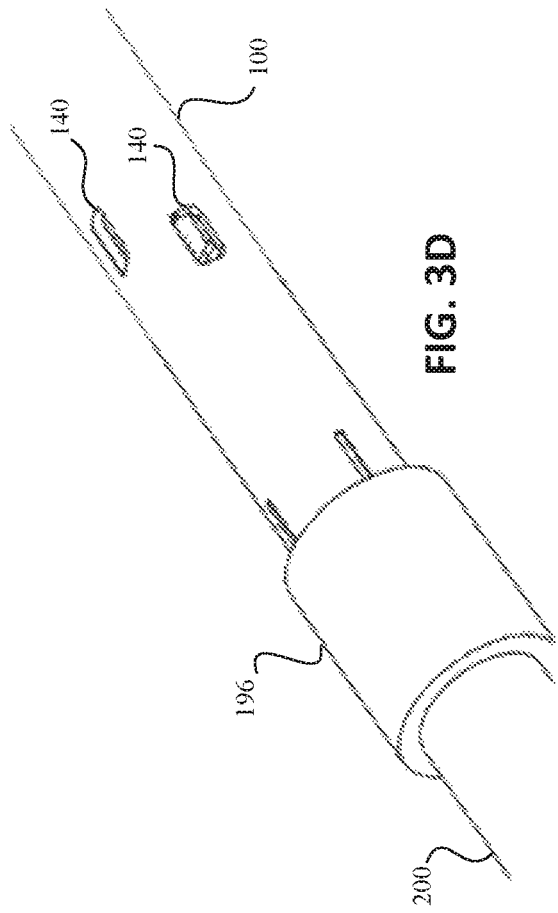
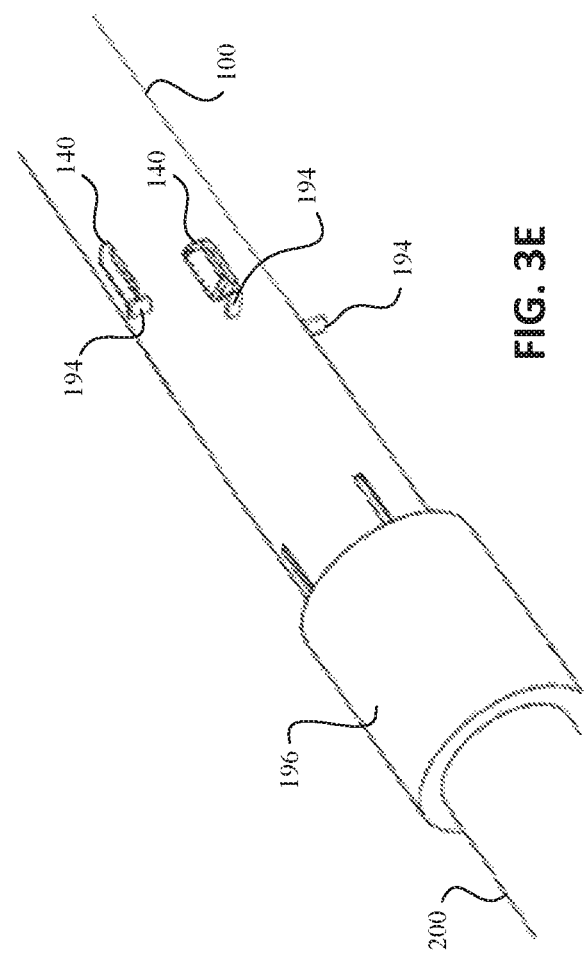

ARTERIAL SHEATH WHICH ALLOWS DISTAL PERFUSION WITHIN A CANNULATED VESSEL

CROSS REFERENCE TO RELATED APPLICATIONS

This application is a continuation of U.S. patent application Ser. No. 15/114,976, which was originally filed on 28 Jul. 2016, and which is incorporated herein by reference in its entirety.

TECHNICAL FIELD

Defining proximal as closer to the heart and distal as further from the heart, aspects of the present disclosure are directed to a sheath having a distal end opening and a proximal end opening; a plurality of fenestrations disposed about portions of the sheath's periphery and length, which are intended to reside within a vessel; and a selectively activatable anchoring assembly configured for maintaining the fenestrations in position substantially immediately or slightly beyond a vessel entry site. When introduced into the vessel, the sheath channels fluid along portions of its length, and perfuses the fluid distally through the fenestrations. The sheath allows vascular access while allowing distal perfusion within the vessel, thereby preventing distal ischemia.

BACKGROUND

Patients with aortic aneurysms may be treated-with self-expandable stent grafts. A sheath having a distal end and a proximal tip is inserted into a vessel such as an artery by way of open surgical or percutaneous puncture, such as through the Seldinger technique. In order to allow the insertion of the stent grafts, the sheath needs to be sufficiently large in diameter. As a result, the sheath itself obstructs blood flow into the extremities and limbs. Such procedures, especially fenestrated or branched abdominal endografts, may be prolonged and the presence of a large vascular sheath in a peripheral vessel e.g., the femoral artery for more than 2 or more hours may result in limb ischemia. There has also been an increase in transcatheter heart valve procedures worldwide. These also involve the insertion of large sheaths into the femoral artery and may last a few hours, thus causing limb ischemia. Hence there is a need for a vascular sheath which allows distal perfusion, while at the same time enabling vascular access for endovascular or transcatheter heart interventions. There are a number of existing ways and approaches that provide for the introduction of sheaths into an artery or vessel, as described hereafter.

U.S. Pat. No. 6,179,813 discloses a vascular access device for infusing fluid into a patient. There are a number of holes along the side of the vascular access device so that the fluid may exit the side holes. There is no concerted fluid flow for perfusing the vessel, nor is there an anchoring element in close relation to the holes, which are not concentrated to be along the path of blood flow, instead being positioned along the entire length of the cannula. In addition, the vascular access device is elongated without the need to be bendable, flexible, or capable of being bent. The incapability of bending will inadvertently create rupture to the artery when the vascular access device is twisted.

U.S. Pat. No. 8,585,679 discloses an apparatus having multiple stages whereby a second stage provides a plurality of fenestrations where blood is directed inwardly axially along the internal portion of a tube. There is additional suction required such that blood can be siphoned away from the heart. The apparatus includes several individual component parts, and is purely meant for use at the heart and not along veins or arteries.

U.S. Pat. No. 5,178,611 describes yet another device as shown in FIG. 4 where there are at least two communication paths adapted to channel fluid outwardly. A first fluid communication path directs flow through at least one fenestration along a portion of the device. A second fluid communication path channels fluid towards a distal end of the device. Thus, there is a need to have at least two fluid communication paths to channel flow within the body. This would also mean a need to have a two-step approach for fluid communication. There is also no anchoring system in relation to the fenestrations.

U.S. Pat. No. 6,099,506 discloses different types of closure seals engaged at an incision to secure a cannula and prevent leakage of blood from the incision. FIGS. 1 to 8 show that the sealing effect must engage both a superficial vessel wall and a wall before entry into the superficial vessel wall.

U.S. Pat. No. 5,542,936 describes a device having anchor flaps, fenestrations, and a way to deploy the anchor flaps. FIGS. 9a and 9b describe an anchor flap used for anchoring the inner wall surface of the vessel. The anchoring of the device may potentially distort the internal profile of the superficial vessel wall, which is highly undesirable. The device has a line of fenestrations on one aspect of the circumference to allow distal perfusion, arranged along the length of cannula (longitudinally). While FIG. 8 seems to suggest that the flow will be disrupted heavily due to the concentration of the flow towards the wall of the vessel especially from fenestrations more proximal to the entry site (i.e., closer to the heart) and not in line with the line of the vessel lumen; there would be turbulent flow which may result in hemolysis (disruption of walls of red blood cells), also creating minimal amount of flow towards the opposite direction.

Because the fenestrations are not circumferential, but only limited to one part of the circumference of the cannula, should the device be inserted in an oblique manner, i.e., not in line or parallel with the course of the vessel, which may occur in certain clinical situations, or be twisted, the fenestrations would direct flow toward the side wall of the vessel, resulting in turbulence, hemolysis and reduced flow.

U.S. Pat. No. 5,843,027 describes a type of construction for enabling an inflatable balloon. The construction and FIG. 1 of the device suggest that there is no uniformity throughout the length of the device. Thus, the device would probably require an undesirably large diameter of entry.

U.S. Pat. No. 6,702,782 introduces a balloon catheter used primarily as a way to anchor a device and prevent unnecessary movement. FIG. 5 expresses that the device is used for removing a blood clot. There is no real requirement for the balloon catheter to be positioned at a particular location. However, the placement of the balloon catheter in an undesirable position can create rupture to the walls of the vessel.

U.S. Pat. No. 6,958,076 describes a venous valve primarily used for fluid flow in a first direction along a defined passageway while a second closed position prevents fluid flow in a backward direction opposite of the first direction. The venous valve is primarily used for allowing one way flow of air into an inflatable cuff. The venous valve is used as a mechanism to allow fluid to flow in only one direction.

U.S. Pat. No. 6,494,909 discloses a one-way valve device used as a replacement valve for use within the human circulatory system.

United States Patent Publication 2009/0259290 primarily introduces a technique to deploy a fenestration segment stent-graft. However, the publication discusses only introduction of the fenestration section to be placed at a branch vessel.

U.S. Pat. No. 6,652,567 discloses a device that addresses a way to repair damaged or diseased blood vessels. The device is designed to introduce a fenestrated vascular graft for repairing the vessel.

U.S. Pat. No. 8,840,636 describes a mesh used for filtering blood flowing within a vessel, where the mesh is meant to entrap embolic materials. The actuation of the mesh structure would stabilize the mesh portion in an anchored position within the vessel.

However, numerous points of contact within the vessel as described would create undesirable effects of contamination.

United States Patent Publication 2008/0294102 discloses a device having a balloon to inflate within the superior vena cava and inferior vena cava. Lateral openings that can presumably be fenestrations are positioned close to an opening, but do not take into account bi-directional flow as seen in FIG. 10. In addition, upon inflation of the balloon, the balloon cannulas seem to show that blood is only perfused in one direction and not bi-directionally. There would be a need to introduce at least two of the devices within the vessel.

U.S. Pat. No. 5,330,433 describes an arterial cannula which includes a diverting side hole which simultaneously perfuses blood to the body and the lower extremity. Two barbs on the cannula exterior position the diverting hole just inside the blood vessel and prevent the back wall of the blood vessel from blocking the diverting hole. However, because these barbs form a fixed protrusion from the otherwise smooth profile of the cannula, insertion of the cannula into the artery—may cause the artery wall to stretch and expand, thereby causing bleeding from around the cannula after insertion, especially if the blood pressure is at a higher level (practitioners in the art will know that bleeding from around the cannula may occur even in patients who are treated with existing standard arterial cannulae having smooth profiles). Because the diverting hole is single thus being limited to one part of the circumference of the cannula, should the device be inserted in an oblique manner, not in line or parallel with the course of the vessel, which may occur in certain clinical situations, or be twisted, the diverting side hole could direct flow toward the side wall of the vessel, resulting in turbulence, hemolysis and reduced flow. The fixed protrusion of the barbs would mandate open surgical removal of the cannula once its purpose is achieved, whereas the defect in a vessel in which a smooth cannula has been placed, after removal of said cannula, may be closed with percutaneous vessel closure devices/techniques currently available in the market.

U.S. Pat. No. 8,795,253 describes a bi-directional perfusion cannula that includes an elongate tube for insertion into an artery. The elongate tube has a first aperture at an end of the tube, an elbow formed in the elongate tube, and a second aperture formed in or slightly rearward of the elbow. The second aperture is the only aperture for distal blood flow, thus the second aperture must be sufficiently large. However, because the elbow forms a fixed protrusion from the otherwise smooth profile of the cannula, insertion of the cannula into the artery may cause the artery wall to stretch and expand, thereby causing bleeding from around the cannula after insertion, especially if the blood pressure is at a higher level (practitioners in the art will know that bleeding from around the cannula may occur even in patients who are treated with standard arterial cannulas with smooth profiles). Because the second aperture is only limited to one part of the circumference of the cannula, should the device be inserted in an oblique manner, i.e., not in line or parallel with the course of the vessel, which may occur in certain clinical situations, or be twisted, the second aperture would direct flow toward the side wall of the vessel, resulting in turbulence, hemolysis and reduced flow. The fixed protrusion of the elbow would mandate open surgical removal of the cannula once its purchase is achieved, whereas the defect in a vessel in which a smooth cannula has been placed, after removal of said cannula, may be closed with percutaneous vessel closure devices/techniques currently available in the market.

PCT publication WO 2014/021786 describes a cannula with multiple fenestrations that are maintainable in position substantially immediately or slightly beyond a site or point of cannula entry into a vessel. The fenestrations enable the simultaneous perfusion of blood into the cannulated vessel along multiple directions, including opposing or anti-parallel blood flow directions relative to a central axis of the cannulated vessel. However, the fenestrations are disposed transversely around the whole of the circumference of the cannula. The arrangement of the fenestrations may weaken the structural integrity of the cannula.

There exists a need in the art to overcome the aforementioned deficiencies of the prior art to improve on the current approaches for introducing and utilizing a sheath in a vessel such as an artery.

SUMMARY

In accordance with an aspect of the present disclosure, a sheath structure configured for cannulating an anatomical vessel includes a first tube having an elongate length, a distal end, a proximal end, and a lumen therebetween for channeling a fluid. The first tube includes: a distal portion coupled to the distal end and configured for receiving an endovascular or transcatheter device; a valve portion disposed near or at the distal end, the valve portion including at least one valve and configured for preventing backflow of a first portion of the fluid out of the distal end; and a first segment configured to entirely reside within the vessel when the vessel is cannulated. The first segment includes: a first lumen therein fluidically coupled to the lumen of the first tube; a proximal opening configured for receiving the fluid from a pumping source and channeling the fluid into the first lumen; and a set of fenestrations disposed distal to the proximal opening and fluidically coupled thereto, the set of fenestrations configured for distally outputting or discharging a second portion of the fluid into the vessel. The pumping source can be a heart or an artificial or mechanical pumping device capable of transferring blood within the vessel. The sheath structure is configured to maintain distal perfusion during an endovascular or transcatheter procedure.

The set of fenestrations is configured for outputting or discharging a second portion of the fluid into the vessel at least one distal flow directions, wherein the at least one distal flow directions has a distal vector flow component parallel to the central axis of the first segment or a central axis of the vessel.

The set of fenestrations can be disposed on at most half of the periphery of the first segment, for instance, at a lower portion of a lower half of the first segment that is intended to face away from a superficial wall of the vessel. The set of fenestrations can include a plurality of fenestrations arranged around a portion of the periphery of the first segment such that a plane through the plurality of fenestrations is at an oblique or a non-oblique angle with respect to a central axis of the first segment. The set of fenestrations can include a first fenestration and a second fenestration, wherein the second fenestration is disposed distally away from the first fenestration.

The first tube further includes a second segment comprising a second lumen aligned with the first lumen, where the second segment is distal to the first segment, and the second segment configured to substantially entirely reside external to the vessel when the vessel is cannulated, wherein the first and second lumens form the lumen of the first tube. The valve portion includes a set of one-way valves disposed in the second segment.

In accordance with an aspect of the present disclosure, the sheath structure further includes an anchoring assembly disposed distally away from the proximal opening and distal to the plurality of fenestrations, where the anchoring assembly includes at least one selectively activatable anchoring element carried by the first segment, which facilitates anchoring of the sheath structure to a superficial wall of the vessel. The at least one anchoring element when activated has a cross sectional area that is larger than a cross sectional area of the first segment at a location of the first segment at which the at least one anchoring structure is disposed.

The at least one anchoring element can include (a) a plurality of petals disposed radially that are selectively displaceable away from or toward the first lumen, (b) a first pressurizable/depressurizable cuff carried by external portions of the first segment, or (c) a second pressurizable/depressurizable cuff or an annular fluid channel carried internal to an external surface of the first segment plus a plurality of anchor members fluidically coupled to or carried by the pressurizable/depressurizable cuff or the annular fluid channel, where the plurality of anchor members is configured to radially expand/contract relative to a central axis of the first lumen in response to pressurization/depressurization of the second pressurizable/depressurizable cuff or the annular fluid channel.

When the at least one anchoring element includes a plurality of petals, the anchoring assembly can be configured for collectively activating the plurality of petals, or selectively activating individual petals within the plurality of petals.

The at least one anchoring element can be arranged such that a plane through the at least one anchoring element is at an oblique or a non-oblique angle with respect to the central axis of the first segment. The anchoring assembly can include a slidable switch or a spring portion activatable for anchoring the sheath structure to the vessel.

The valve portion is adapted to expand to allow insertion of a second tube into the first tube. The second tube can include a dilator adapted to protrude through the valve portion into the lumen of the first tube. The second tube can further include a self-expandable stent graft adapted to expand after insertion into the vessel.

The first tube can include at least one graduated scale disposed along the elongate length thereof. The first tube can include a plurality of visible markings on an exterior surface thereof, the plurality of visible markings positioned on the first tube in a manner that corresponds to the distribution of the set of fenestrations on the first segment. The sheath structure can further include a fluid indicator port disposed on the first segment, which is coupled to a translucent or transparent fluidic channel configured for providing a visual indication of the presence of fluid into the fluid indicator port. The channel can include a luminous portion that carries therein a substance which when reacted with blood/fluid causes the blood/fluid to visually appear brighter.

BRIEF DESCRIPTION OF THE DRAWINGS

FIG. 2A to FIG. 2D are schematic illustrations of a first tube or sheath having multiple fenestrations in accordance with an embodiment of the present disclosure.

FIG. 3A to FIG. 3E are magnified schematic illustrations of portions of the first tube or sheath according to the illustrations of FIG. 2A to FIG. 2D.

DETAILED DESCRIPTION

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith.

The use of "/" in a FIG. or associated text is understood to mean "and/or" unless otherwise indicated. The recitation of a particular numerical value or value range or the use of terms such as approximately or about is understood to include or be a recitation of an approximate numerical value or value range (e.g., within +/−2%, +/−5%, +/−10%, +/−15%, or +/−20%).

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p.

140), by Peter J. Eccles, Cambridge University Press (1998)). In general, an element of a set can include, be, or be a portion of a system, an apparatus, a device, a structure, an object, a process, a physical parameter, or a value depending upon the type of set under consideration.

As used herein, proximal is defined as toward or closer to the heart, and distal is defined as further away from the heart or in a direction away from or opposite to distal with respect to fluid flow. The term "vessel" is taken to mean an anatomical vessel, passage, or channel (e.g., a blood vessel, such as an artery) of a patient or subject, or an anatomical chamber or compartment. The term "perfusion" is taken to mean the injection, transfer, or communication of blood and/or one or more other fluids into a vessel for purpose of enabling the blood and/or other fluid(s) to reach an organ or tissues (e.g., to supply nutrients and oxygen thereto). The term "fluidically coupled" is taken to mean coupled in a manner that provides for fluid (e.g., liquid/gas) transfer or communication.

Figure 1A:
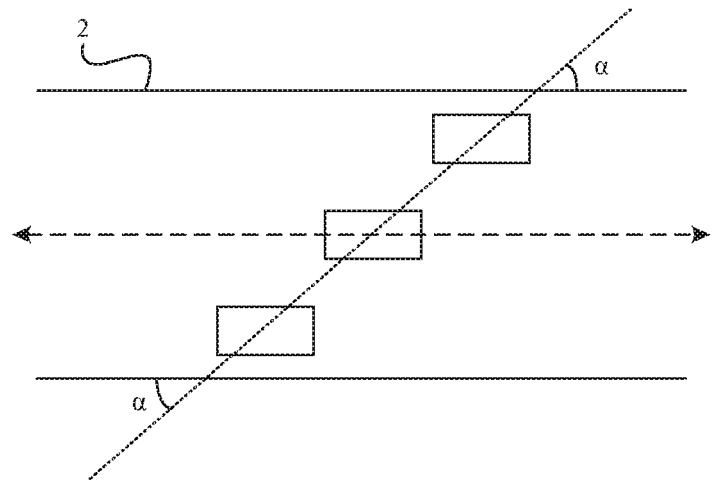
FIG. 1A and FIG. 1B are diagrams showing a representative oblique arrangement in accordance with the present disclosure.
Figure 1B:
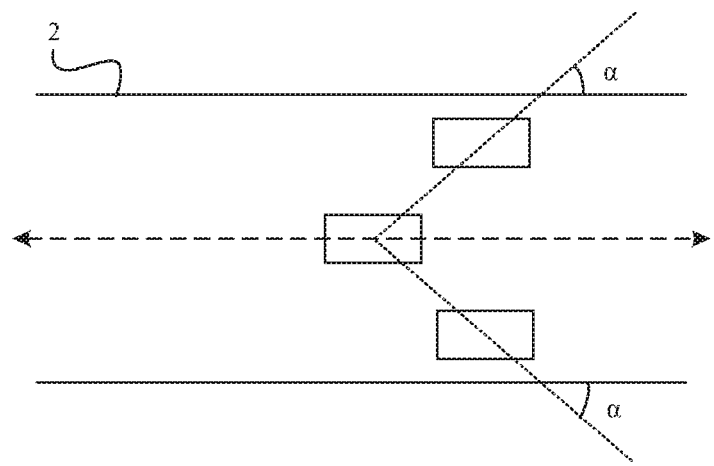

The term "oblique" or "obliquely" is taken to mean at an angle that is neither a right angle nor a multiple of a right angle relative to or along a lengthwise reference segment, section, or axis (e.g., a central longitudinal axis or a peripheral edge, border, or boundary) of a vessel or a tubular structure disposed therein, and/or a direction of fluid flow (e.g., distal fluid flow) in the vessel or tubular structure. Representative examples of oblique arrangements or orientations of structures within a tubular structure or vessel 2 are shown in FIG. 1A-FIG. 1B. An angle that is oblique can be measured relative to a lengthwise/longitudinal/central axis or a fluid flow direction of the vessel 2 and a line or plane defined across or through the tubular structure or vessel 2, for instance, a line or plane corresponding to the positions of a plurality of structures carried by the tubular structure or vessel 2. An individual having ordinary skilled in the art will readily understand that various oblique arrangements or orientations are possible in accordance with embodiments of the present disclosure.

Figure 1C:
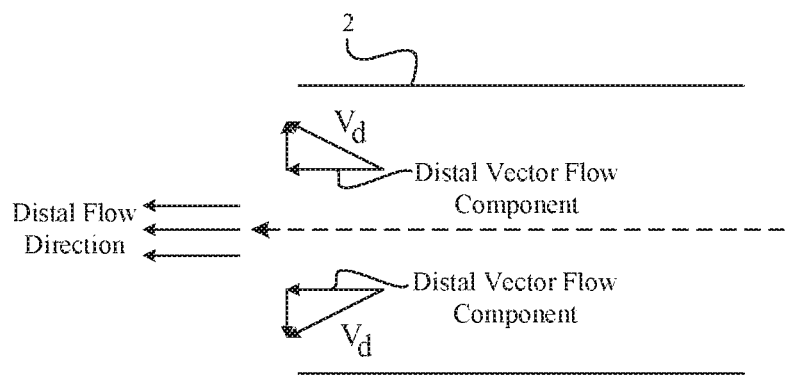

The term "distal vector flow component" means a distally directed component of a fluid flow vector $V_d$ within a vessel 2, where distally directed is defined as a direction that is parallel to a lengthwise/longitudinal/central axis of the vessel 2 along which fluid can flow in the vessel 2. Representative distal fluid flows, distal fluid flow vectors $V_d$, and distal fluid flow components with respect to a representative vessel 2 are illustrated in FIG. 1C.

Embodiments in accordance with the present disclosure are directed to a sheath, sheath structure, or sheath device (e.g., an arterial sheath) providing (a) an entry opening or opening at a proximal sheath portion, segment, end, or tip that is configured for insertion into a vessel (e.g., an artery) at a cannulation site or point, and which is configured for displacement or travel along the vessel and positioning away from the cannulation point; and (b) a set of fenestrations, apertures, or openings configured to be positioned or maintained in position essentially or substantially immediately beyond the cannulation point. Most embodiments include multiple fenestrations. The sheath is configured to receive a flow of blood/fluid at or into the proximal entry opening and channel the blood/fluid along a least resistive pathway through a lumen of the sheath with considerable laminar flow in a first direction or first set of directions distally away from the heart when portions of the lumen are positioned within the vessel. Blood/fluid flowing through the lumen is distally directed out of the lumen into the vessel by way of the fenestrations in multiple distal directions, such as a second set of directions. More particularly, a first portion of blood/fluid that is received from the proximal entry opening is directed into portions of the lumen in one or more particular flow directions distally away from the heart, such as a first flow direction or a first set of flow directions; and a second portion of the blood/fluid is discharged from the lumen through the set of fenestrations into the vessel in one or more additional flow directions, distally away from the heart, such as a second set of flow directions.

Figure 2A:
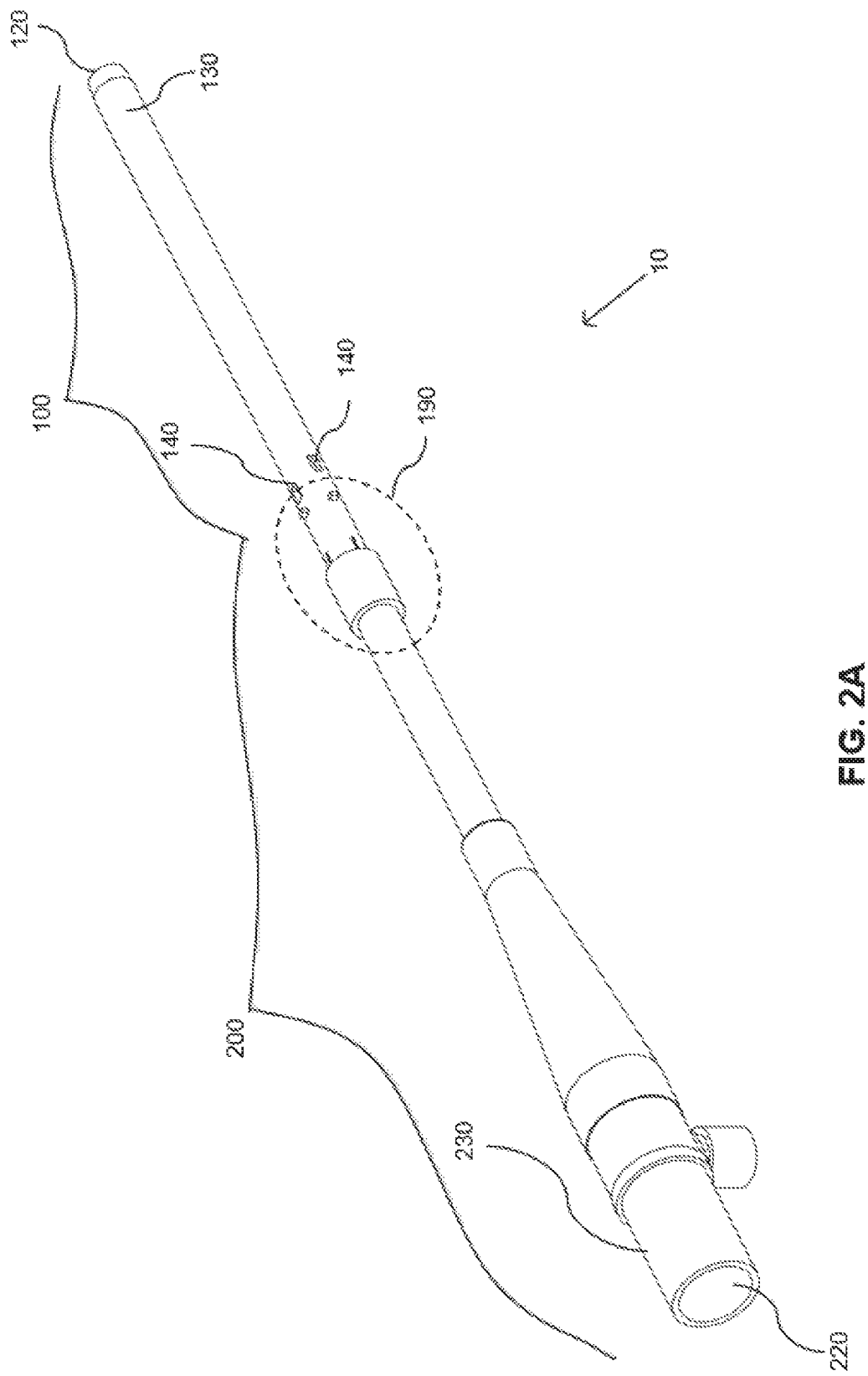
Figure 2B:
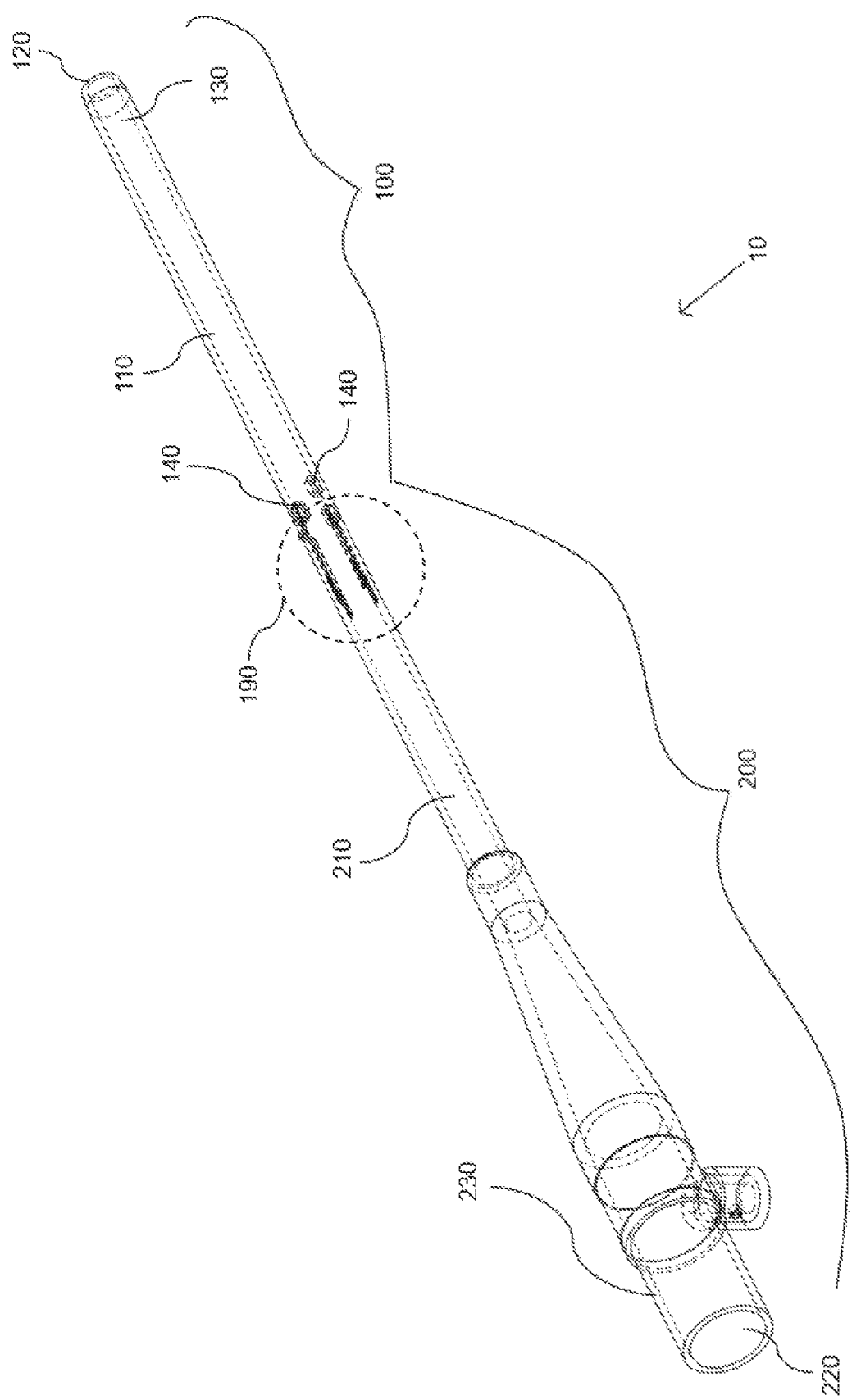

FIGS. 2A-12B are schematic illustrations showing portions of a sheath assembly, sheath structures, sheath device, or sheath (e.g., an arterial sheath) in accordance with particular representative embodiments of the present disclosure. As indicated in FIG. 2A, FIG. 2C, and elsewhere, in an embodiment the sheath includes at least a first tube, tubular member, or tubular structure 10 providing a lumen therein/therethrough and having a first elongated segment 100 coupled to a second elongated segment 200, where the second segment 200 is distal to the first segment 100. In multiple embodiments, the first tube 10 is a continuous tube that includes a lumen (e.g., a continuous lumen) therein/therethrough, and which lacks physically segregated or segregatable segments. Hence, segments 100, 200 in accordance with the present disclosure can be defined with respect to particular portions or fractions of the length of the tube 10.

The first segment 100 spans, extends along, or defines an elongate first fraction of the length of the first tube 10; and the second segment 200 spans, extends along, or defines a second fraction of the first tube's length. The first and second segments 100, 200 are coupled, joined, or formed (e.g., integrally formed) together. The first segment 100 includes at least one proximal opening 120 disposed at, along, adjacent, or contiguous to a proximal portion, segment, end, or tip 130 of the first tube 10. In various embodiment, the proximal tip 130 is tapered in order to facilitate smooth insertion into a vessel. The second segment 200 includes a distal opening 220 disposed at, along, adjacent, or contiguous to a distal portion, segment, end, or tip 230 of the first tube 10. An individual having ordinary skill in the art will readily understand that the first tube 10 can itself be defined as the sheath, and hence the second segment's distal opening 220 can be identified or defined as the sheath's distal opening 220, and the first segment's proximal opening 120 can be defined as the sheath's proximal opening 120.

As indicated in FIGS. 2B, 2C, 3B, and 3C, the first segment 100 includes a first lumen 110 therein/therethrough, which forms a first portion of the first tube's lumen. The second segment 200 includes a second lumen 210 therein/therethrough, which forms a second portion of the first tube's lumen. The first lumen 110 is coupled (e.g., integrally and fluidically coupled) to the second lumen 220, which is contiguous or aligned with the first lumen 110. Correspondingly, the first segment 100 and the second segment 200 are joined or formed (e.g., integrally formed) together to form a passage or pathway (e.g., a continuous pathway) corresponding to the first and second lumens 110, 220.

The first segment 100 is configured for entering into a vessel (e.g., an artery) at a cannulation site or point, and positioning within/displacement along the vessel such that the proximal end 130 of the first tube 10 resides at an intended or predetermined distance away from the cannulation point. Blood/fluid is intended to be received from the proximal opening 120 and directed into the first lumen 110 along a first distal flow direction or first set of distal flow directions (i.e., going away from the heart). The first segment 100 carries a plurality of openings, apertures, windows, or fenestrations 140, which are fluidically coupled to the proximal opening 120 by way of the first lumen 110.

Thus, the first lumen 110 enables blood/fluid flow from the proximal opening 120 distally toward, to, and through the fenestrations 140.

Once the first segment 100 has been positioned in the vessel, the fenestrations 140 are intended to reside near/very near/slightly or very slightly proximal/adjacent to the cannulation point. Blood/fluid flowing in the vessel is received by the proximal opening 120 and channeled distally through the first lumen 110. A portion of such distally channeled blood/fluid travels distally toward the first tube's distal end 230; and another portion of the blood/fluid channeled distally through the first lumen 110 is discharged from the first lumen 110 through the set of fenestrations 140 towards the limb, head (in the case of neck vessel cannulation), or other distal region. Thus, a first portion of the blood/fluid can be distally channeled in a first direction or first set of directions from the proximal opening 120 into the first tube's lumen, while a second portion of the fluid can be distally channeled towards, to, and through the fenestrations 140 and output from the fenestrations 140 into the vessel in a second set of distal directions. The blood/fluid that is discharged from the fenestrations 140 into the vessel has a distal vector flow component that is parallel to a lengthwise/longitudinal/central axis of the first segment 100 and/or a lengthwise/longitudinal/central axis of the vessel. The fenestrations 140 thus provide fluid exit sites, ports/portals, or points by which blood/fluid that enters the first tube 10 by way of the proximal opening 120 can be distally discharged from the first segment 100 while the first segment 100 resides within the vessel. A sheath in accordance with the present disclosure is able to maintain distal blood flow within the cannulated vessel, and as a result, the risk of ischemia in the extremity or head in the case of neck vessel cannulation is substantially or greatly reduced, or essentially eliminated.

Figure 3A:
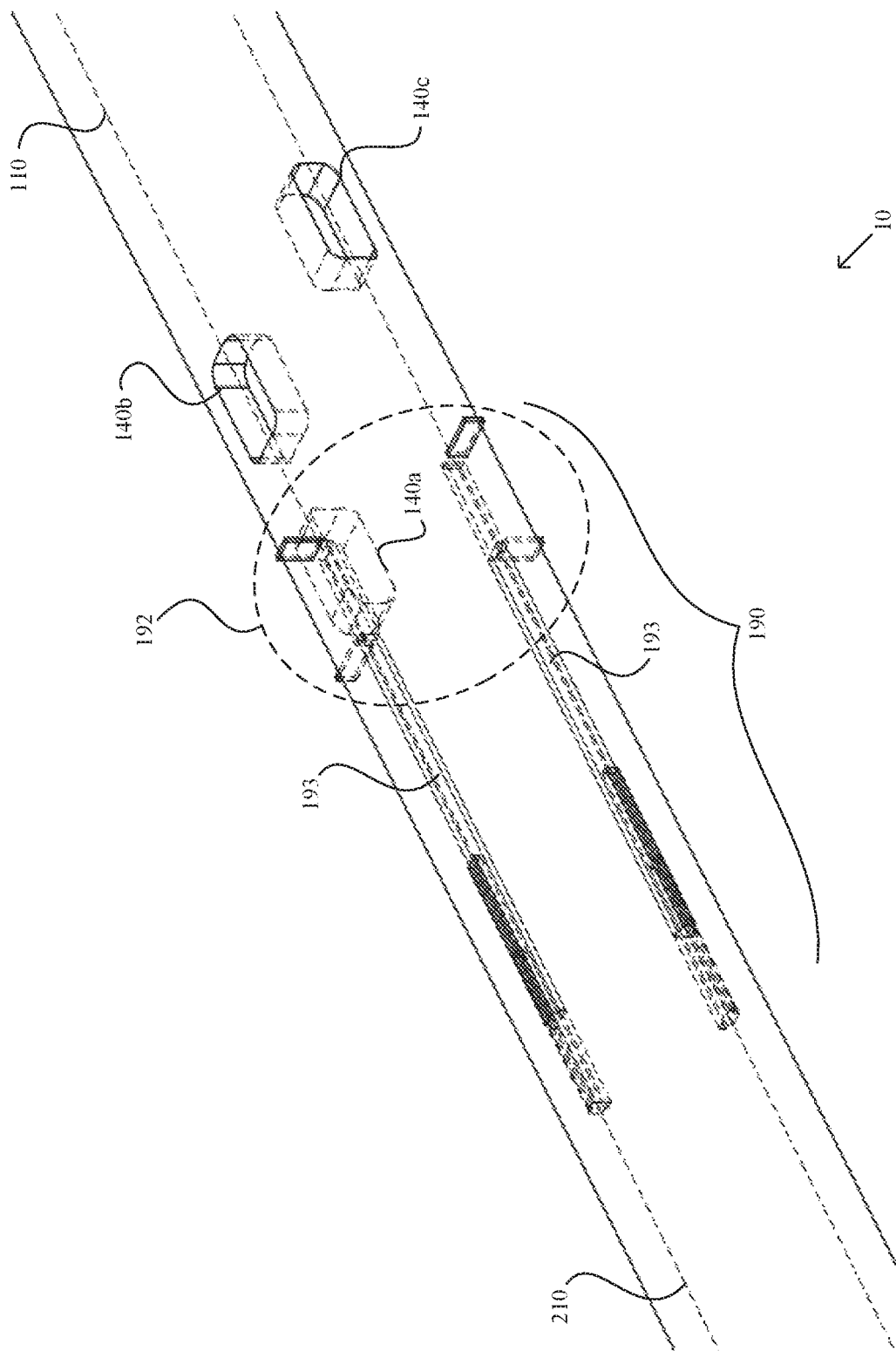

FIG. 3A to FIG. 3E illustrate fenestrations 140 disposed along the portions of the length of the first segment 100 and around portions of a cross-sectional area, periphery, or circumference of the first segment 100 in accordance with a representative embodiment of the present disclosure. More specifically, in various embodiments the fenestrations 140 are disposed obliquely around a portion of the circumference of the first segment 100. As such, as indicated in FIG. 3B-3C, a plane through a plurality of fenestrations 140 (e.g., a subset of fenestrations 140 or each fenestration) forms a non-parallel and non-perpendicular angle, i.e. an oblique angle α that is neither a right angle nor a multiple of a right angle, with respect to the axial direction of the first lumen 110. In some embodiments, the angle α formed by the plane of the set of fenestrations 140 is 45° relative to the axial direction or fluid flow direction of the first segment 100. It would be apparent to a person having ordinary skill in the relevant art that other angles α are possible, such as between 30° and 60°.

Referring to FIGS. 3B and 3C, compared to a non-oblique or perpendicular arrangement of fenestrations, an oblique arrangement of fenestrations 140 means that the plane through the plurality of fenestrations 140 is more parallel to the axial direction or lengthwise/longitudinal/central axis of the cannulated vessel. An oblique arrangement of the set of fenestrations 140 advantageously facilitates more streamlined distal flow of blood/fluid from the fenestrations 140 into the vessel as compared to a non-oblique/perpendicular fenestration arrangement, thereby improving the efficacy and efficiency of distal blood dispersal towards distal extremities and limbs of the patient. Additionally, an oblique arrangement of fenestrations 140 can result in enhanced structural integrity of the first segment 100 compared to a non-oblique fenestration arrangement, depending upon the number of fenestrations 140 carried by the first segment 100.

In some embodiments having an oblique arrangement of fenestrations 140 about and along portions of the first tube's first segment 100, two or more fenestrations 140 need not be disposed on a plane in a linear manner relative to each other; rather, two or more fenestrations 140 can be disposed in a helical or spiral arrangement along and about the first segment 100. Consequently, a projection of a helical/spiral curve corresponding to the locations of the fenestrations 140 onto the first segment's longitudinal axis forms an oblique angle α that is neither a right angle nor a multiple of a right angle with respect to this longitudinal axis.

In various embodiments, the fenestrations 140 are slightly or very slightly proximal or proximally adjacent/contiguous to a set of anchoring elements or structures provided by an anchoring assembly 190, as further detailed below. In a representative embodiment including three fenestrations 140a-c disposed in an oblique arrangement such as shown in FIG. 3A-3E, a first fenestration 140a can be positioned closest to the distal opening 220 of the second segment 200 (and hence is the most distal fenestration 140 carried thereby); the second fenestration 140b can be proximal to the first fenestration 140a, and the third fenestration 140c can be proximal to the second fenestration 140b.

Fenestrations 140 can be disposed about or around the periphery, cross-sectional area, or circumference of the first segment 100 in a variety of manners in embodiments that exhibit non-oblique or oblique fenestration arrangements. In some embodiments, fenestrations 140 are not or need not be excluded from particular portions of the cross-sectional area/periphery/circumference of the first segment 100; however, in several embodiments, fenestrations 140 are excluded from certain portions of the first segment's cross-sectional area/periphery/circumference, and thus are only partially disposed relative to the entire periphery of the first segment 100, such as along, or at a particular fraction or section of the first segment's cross-sectional area, periphery, or circumference.

In certain embodiments, fenestrations 140 reside in each of a first or upper half of the first segment's cross-sectional area/periphery/circumference and a second or lower half of the first segment's cross-sectional area; however, in other embodiments, fenestrations 140 reside or approximately reside only in a particular half (e.g., the lower half) of the first segment's cross-sectional area/periphery/circumference. In addition, depending upon embodiment details, each fenestration 140 can have an identical cross-sectional area and/or shape, or some fenestrations 140 can have different cross-sectional areas and/or shapes relative to other fenestrations 140 (e.g., particular fenestrations 140 can have different dimensions compared to one or more other fenestrations 140).

Figure 4A:
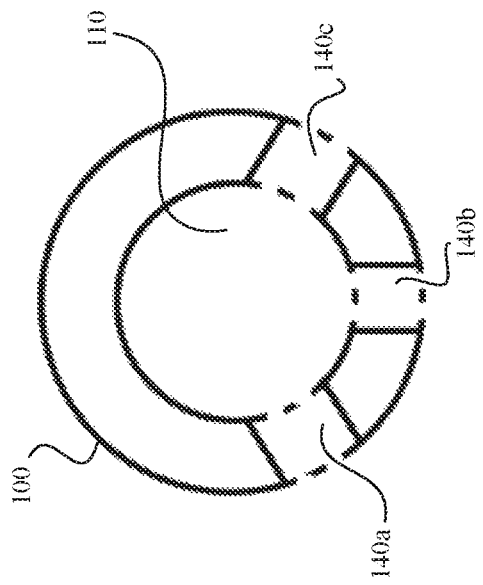
FIG. 4A to 4C are schematic cross-sectional illustrations showing representative arrangements of fenestrations in accordance with an embodiment of the present disclosure.
Figure 4C:
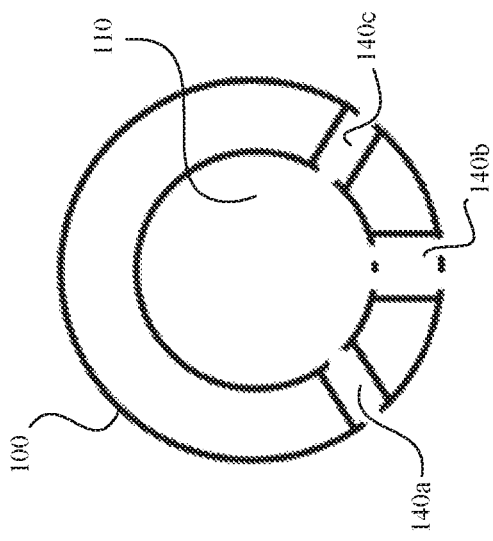
Figure 4B:
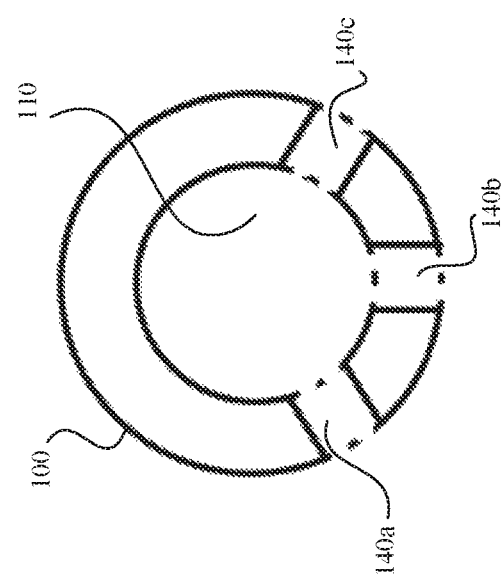

FIG. 4A-4C show cross sectional views of the first segment 100 of the first tube 10 and a plurality of fenestrations 140 carried thereby in accordance with representative embodiments of the present disclosure. For purpose of simplicity and to aid understanding, in this representative embodiment the first segment 100 includes a first fenestration 140a, a second fenestration 140b, and a third fenestration 140c. It can be seen from FIG. 4 that the fenestrations 140 are not disposed or uniformly disposed around the entire or complete cross-sectional area/periphery/circumference of the first tube 10. Rather, the arrangement of the fenestrations 140 is such that approximately or up to at most half of the cross-sectional area/periphery/circumference of the first segment 100 carries or contains the fenestrations 140, while other portions of the cross-sectional area/periphery/circumference of the first segment 100 excludes fenestrations 140. For instance, the fenestrations 140 can be disposed in a lower or downward facing/downwardly oriented half of the first segment's cross-sectional area/periphery/circumference, where "lower" or "downward facing"/"downwardly oriented" refers to portions of the first segment 100 that are opposite to and face away from the site or point at which the first segment 100 entered into the vessel; and fenestrations 140 do not reside in the corresponding/counterpart upper half of the first segment's cross-sectional area/periphery/circumference (i.e., the upper half excludes fenestrations 140).

For instance, the first fenestration 140a can be disposed at or approximately at a lower left portion of the cross-sectional area or circumference of the first segment's lower half; the second fenestration 140b can be disposed at or approximately at a bottom portion of the cross-sectional area or circumference of the first segment's lower half; and the third fenestration 140c can be disposed at or approximately at a lower right portion of the cross-sectional area or circumference of the first segment's lower half. The fenestrations 140a-c are thus carried by or disposed on (e.g., only carried by or disposed on) a lower or downwardly oriented region of the lower half section of the cross-sectional area or circumference of the first tube's first segment 100, while other portions (e.g., the upper half) of the cross-sectional area or circumference of the first tube 10 exclude or do not contain fenestrations 140.

If a sheath that includes fenestrations 140 carried on the upper half of the first segment's cross-sectional area, periphery, or circumference were inserted into a vessel, portions of at least some of the fenestrations 140 carried by this upper half section would face upward, toward the vessel's superficial wall 4. Distal blood/fluid flow through such fenestrations 140 is less efficient than for fenestrations 140 that at least partially face in a downward generally downward, or at least somewhat downward direction, away from the cannulation site, and/or which at least partially face in a distal direction. By limiting the positions of fenestrations 140 to approximately or at most a lower half of the cross-sectional area, periphery, or circumference of the first segment 100, and in particular lower portions of the lower half of the cross-sectional area, periphery, or circumference of the first segment 100, blood/fluid flow out of the set of fenestrations 140 in the distal direction is increased and/or more efficient. Furthermore, such an arrangement of fenestrations 140 in only a particular half (e.g., the lower half) or region of the first segment 100 can enhance the structural integrity of the first segment 100, as there are fewer openings therein that can reduce the first segment's structural integrity.

It will be apparent to an individual having ordinary skill in the relevant art that the number of fenestrations 140 disposed in a predetermined half-portion of the first segment's cross-sectional area, periphery, or circumference is not limited to three; there can be fewer than or more than three fenestrations 140 disposed in such a manner. It will be apparent to such an individual that the fenestrations 140 can also be arranged to reside around more than a half portion of the cross-sectional area, periphery, or circumference of the first segment 100, such as three-quarters thereof, depending upon embodiment details.

Each fenestration 140 is configured or adapted to provide an intended shape, size, or blood/fluid communication area, and not all fenestrations 140 need to have an identical shape, size, or blood/fluid communication area as indicated in FIGS. 4A and 4C. The shape(s) and/or dimension(s) of particular fenestrations 140 can be defined relative to the shape(s) and/or dimension(s) of other fenestrations 140 carried by the first segment 110 (e.g., made larger or smaller, depending upon the position(s) of certain fenestrations 140 relative to other fenestrations 140) in order to provide an intended distal blood/fluid flow or output relative to an expected proximal blood/fluid flow or output, and/or an intended, target, or desired degree of structural integrity. In a representative embodiment, a ratio of a total fenestration area through which blood/fluid can exit the fenestrations 140 (e.g., a total cross sectional area for blood/fluid flow provided by the fenestrations 140) to a total proximal exit opening area through which blood/fluid can exit the first tube's proximal exit opening 120 is not less than 10% and typically between 10% to 600% (e.g., 20% to 50%, 25% to 45%, or 30% to 40%).

Figure 5:
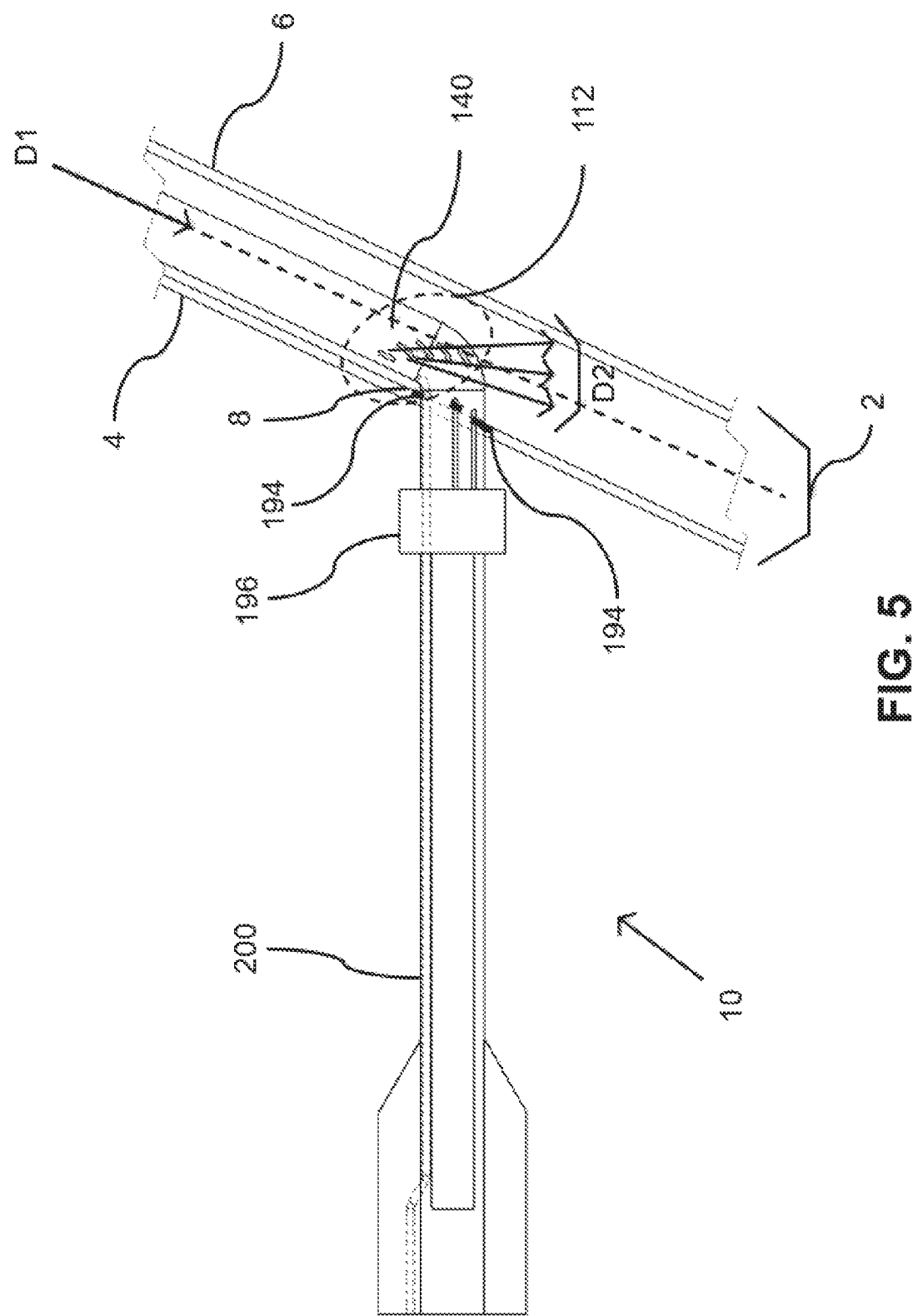
FIG. 5 is a representative illustration showing portions of first and second segments of a first tube or sheath positioned relative to a vessel entry site by which a first segment of the first tube has been positioned within a vessel.

FIG. 5 is a schematic illustration of a representative sheath positioned within a vessel 2 in accordance with an embodiment of the present disclosure. When the sheath is in use such that blood/fluid can flow or is flowing into the first tube's proximal opening 120, the first segment 100 is configured to reside entirely within the vessel 2. The second segment 200 is configured to almost or essentially entirely reside external to the vessel, 2 outside of the patient's body. For instance, when the sheath is in use, only a small portion of the second segment 200 that is distal to the fenestrations 140 and which is proximal to the inner surface of the cannulated vessel's superficial wall resides within the vessel 2. The first segment 100 is flexible or pliable along at least portions of its length, and the second segment 200 is at least generally or somewhat flexible or pliable along portions of its length.

Figure 6A:
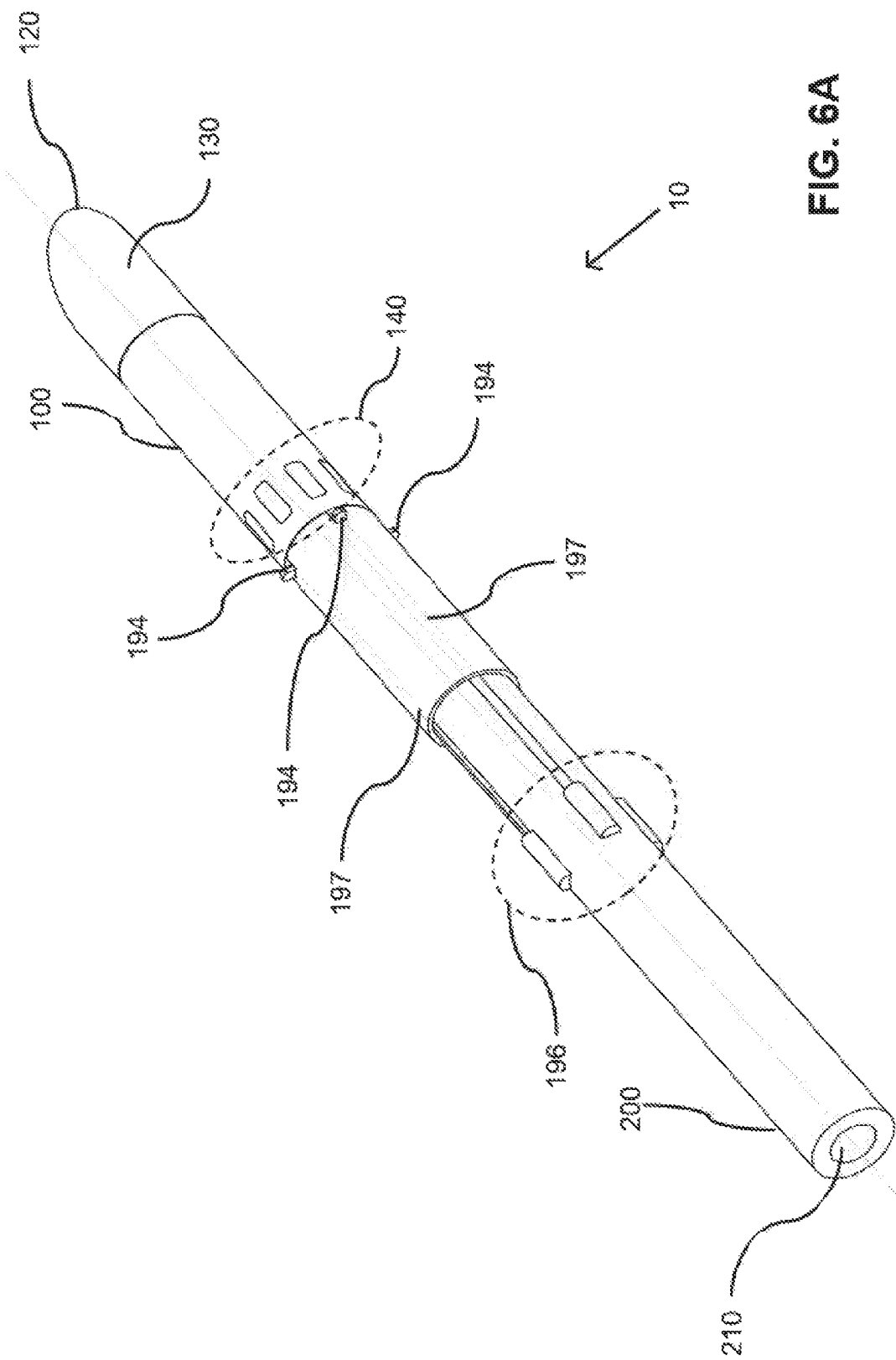
FIG. 6A to FIG. 6C are schematic illustrations of a sheath having multiple fenestrations and an anchoring assembly in accordance with an embodiment of the present disclosure.
Figure 6B:
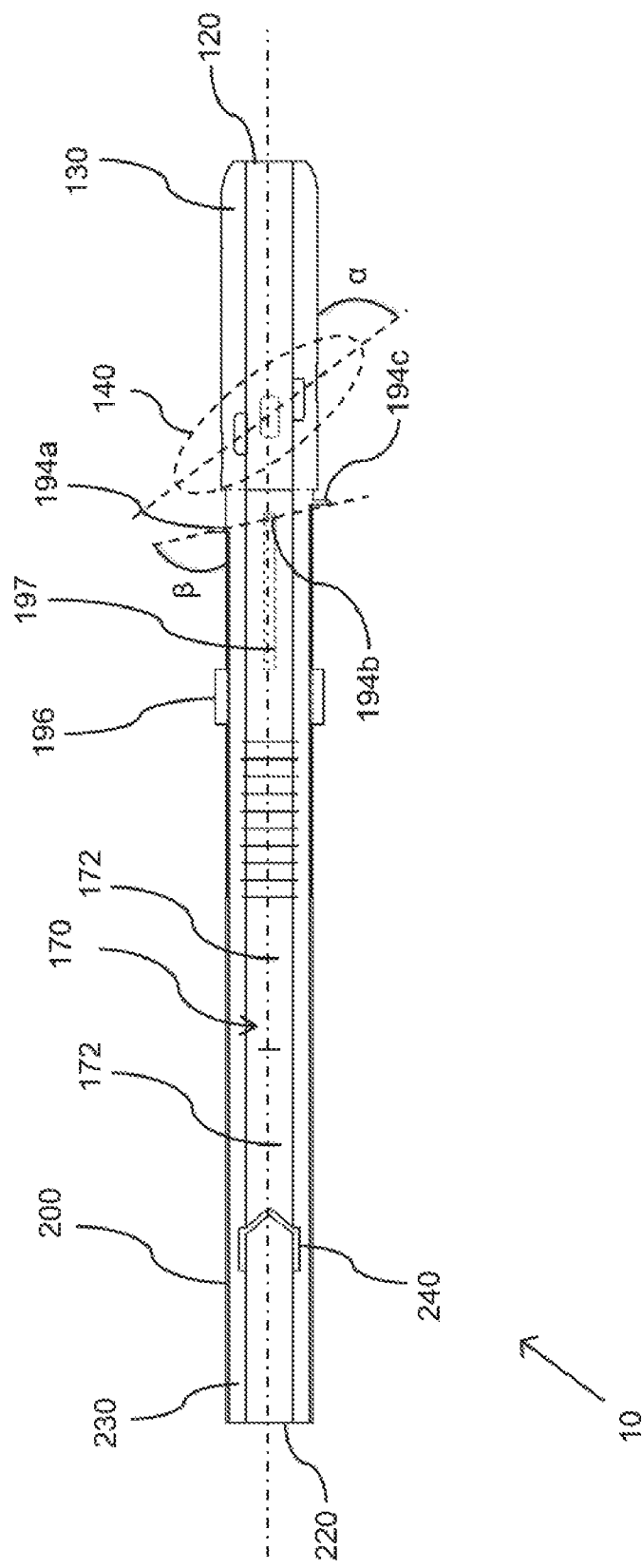
Figure 6C:
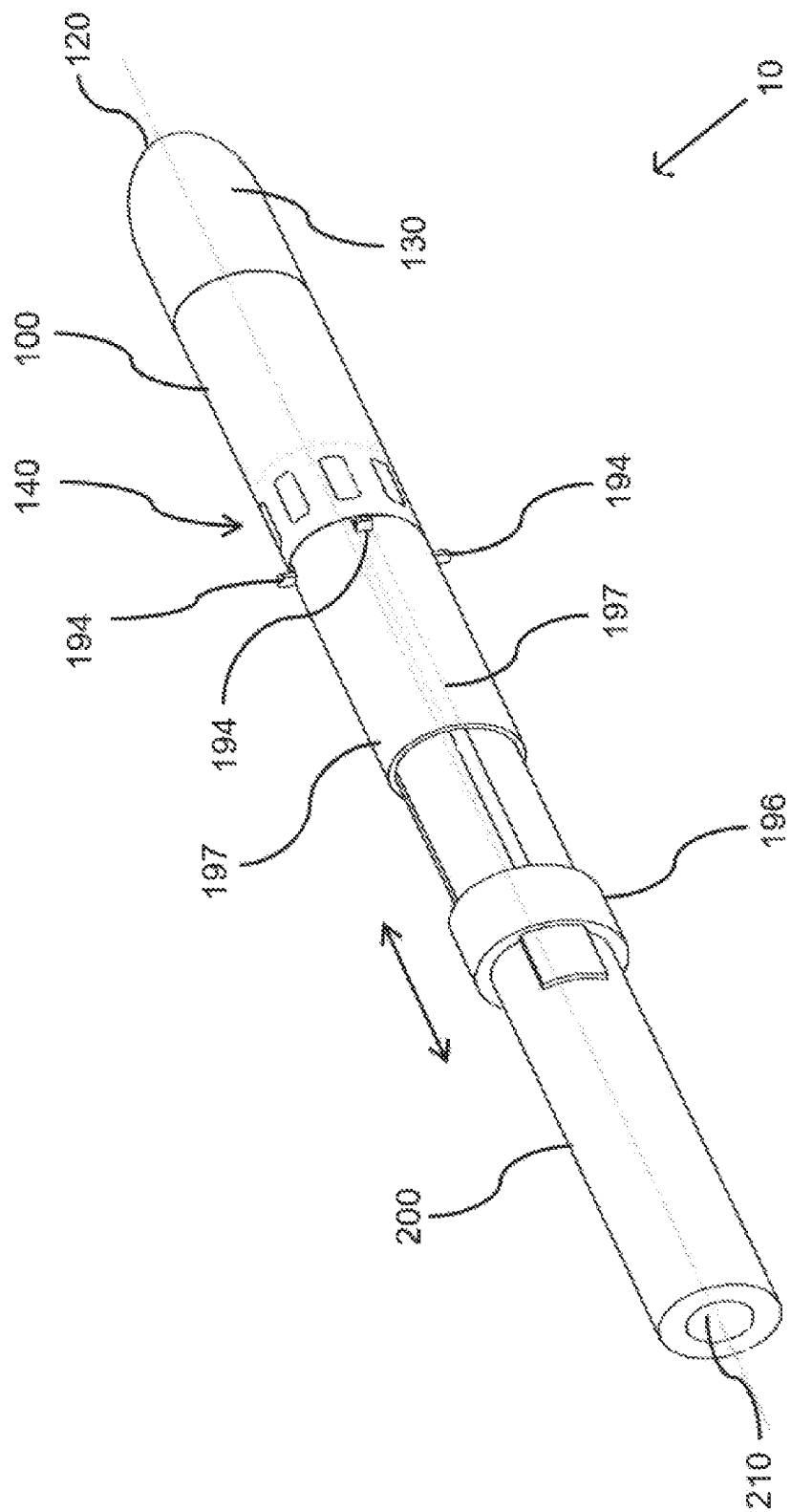

FIG. 6A-FIG. 6C illustrate an anchoring assembly 190 carried by the first tube 10 in accordance with particular embodiments of the present disclosure, where the anchoring assembly 190 includes at least one anchoring element or structure such as a number of anchoring members 192 that are selectively activatable or displaceable to facilitate or enable retention, maintenance, or anchoring of the first tube 10 in an intended position and an intended orientation within the cannulated vessel. In a number of embodiments, a boundary or dividing line between the first segment 100 and the second segment 200 can be established or defined with respect to a predetermined edge or border of a particular anchoring member 192, a given subset of anchoring members 192, or the anchoring members 192 considered collectively (e.g., depending upon the arrangement of anchoring members 192). For instance, a boundary between the first and second segments 100, 200 can be defined relative to or as a distal border or edge of a distal-most anchoring member 192 in a manner indicated FIG. 3C, or in an analogous manner that will be understood by an individual having ordinary skill in the relevant art. The anchoring assembly 190 and anchoring members 192 are configured to facilitate clinician positioning or disposition of the fenestrations 140 at an intended position within the cannulated vessel, as further detailed below.

In a number of embodiments, the anchoring assembly 190 includes at least one switch 196, such as a slidably displaceable structure/switch coupled or connected to the anchoring members 192 by way of thin, flexible/deformable metal strips or plastic strips 193 or any suitable flexible material for providing or forming the anchoring members 192. The anchoring members 192 can include or be a set of protrusions or petals 194 that are coupled to or formed from portions of the strips of material 193 (e.g., end or tip portions of the strips of material) that can be displaced outwardly/ radially away from the first lumen 110 and abut or anchor onto the inside surface or superficial wall of the cannulated vessel. The terminal end portions or ends of the petals 194 can be blunt or curved in order to minimize the risk of damaging the vessel, in a manner readily understood by an individual having ordinary skill in the relevant art.

The strips 193 are configured to lie or reside in one or more shallow (e.g. generally flat, suitably profiled, etc.) tunnels/slots/spaces within the wall of the first tube 10, terminating just distal to the fenestrations 140, where the wall includes a narrow space portion, slit, slot, ramp, bump, recess, and/or defect (e.g., an intentionally thinned/puncturable area) therein. Each of the strips 193 when retracted is housed or positioned within an encasement or space portion 195 of the first tube 10, which includes or is a narrow tunnel/slot in the first tube's wall. The strips 193 can be positioned (e.g., within a capsule or capsule type structure) in a first position whereat the petals 194, which are at the terminal ends of the strips 193, are unactuated/undeployed/unactivated, such that the petals 194 remain internal to or below the exterior surface of the first segment 100 (i.e., the petals 194 do not extend or protrude beyond the exterior surface of the first segment 100 when in the first position, and remain in the space portions 195).

The user/clinician can displace or actuate the switch 196 (e.g., by way of slidably displacing the switch) to effectuate or activate the petals 194 and transition the strips 193 from the first position to a second position, such that the petals 194 are correspondingly displaced to protrude or extend outwardly from the space portions 195 in a radial manner. When at the second position, the petals 194 extend beyond the exterior surface of the first segment 100 and can abut or anchor onto the superficial wall of the cannulated vessel. Thus, when at the second position, a maximum cross-sectional area, circumference, or diameter provided or defined by the petals 194 exceeds the outer cross-sectional area, periphery, circumference, or diameter of the first segment 100 (e.g., where the petals 194 exit the first segment 100). The activated anchoring assembly 190, together with the activated anchoring members 192 (in this case, the petals 194) facilitates or enables retention, maintenance, or anchoring of the sheath in an intended position within cannulated vessel, such that the fenestrations 140 are in position to distally direct blood/fluid flow.

A portion of the first tube 10, such as a section of the first tube 10 corresponding to the space portions 195, can include a resistance portion or abutment 197 positioned distal to the fenestrations 140, which can prevent accidental displacement of the fenestrations 140 outside of the vessel wall. The resistance portion 197 can correspond to or form outer walls of the space portions 195. The resistance portion 197 can be seamlessly joined with a portion of a circumference of the first tube 10 just distal to the fenestrations 140. The resistance portion 197 can be non-movable. The resistance portion 197 provides resistance so that each of the petals 194 can be forced to expand outwardly through or from the space portions 195 in the wall. Alternatively, the resistance portion 197 can be made movable in accordance with manufacturing methods. The resistance portion 197 can be pre-fabricated/molded/formed such that the diameter of the first tube 10 is the same throughout. A portion of the resistance portion 197 can be adapted to provide at least one friction point or region, thereby providing resistance to prevent accidental movement or displacement of the fenestrations 140.

When the anchoring assembly 190 is actuated or activated, each petal 194 positioned within a space portion 195 of the wall of the first tube 10 is configured to expand or protrude outwardly (e.g. radially or transversely away from a lengthwise/longitudinal/central axis that extends through the first tube 10) through or from the space portions 195. A person having ordinary skill in the art will readily understand the space portions 195 and the slots/slits/recesses/defects provided thereby that the petals 194, when actuated, protrude outwardly/radially from openings in the first tube 10. The space portions 195, where the strips 193 are configured to lie or reside in one or more tunnels within the wall of the first tube 10, provide a set of guides such that each of the petals 194 is forced to translate and expand outwardly/radially through, from, or out of its space portion 195 in a desired (e.g., uniform) manner. The guides act as railings whereby the petals 194 are slidably displaceable along portions of the length of the guides.

In a number of embodiments, the strips 193 include or are flexible, outwardly bendable strips of material peripherally or circumferentially disposed about at least one space portion 195 of the first tube 10. An individual having ordinary skill in the art will appreciate that a vessel of a child or women is more likely to be smaller than a vessel of a man. Thus, the clinician would have informed knowledge of an appropriate amount or degree of outward expansion prior to effectuating the set of petals 194. In relation to the sheath having a predefined diameter suitably dimensioned according to the patient's expected or actual vessel size, a maximum size, cross-sectional area, circumference, or diameter of the expanded or activated set of petals 194 when expanded outwardly within the patient's vessel is approximately 10% to 30% larger than the outer diameter of the sheath (e.g., where the petals 194 exit the sheath). More generally, the expanded diameter of the petals 194 is larger than the outer diameter of the first segment 100. A person skilled in the art will readily understand that the height of each of the set of petals 194 can vary in accordance with the size/diameter of the vessel.

The switch 196 can be configured to slide along portions the first tube 10, specifically the second segment 200. The second segment 200 includes a set of grooves which match a set of teeth or bumps on the switch 196. Each of the grooves coincides with a corresponding tooth/bump. The grooves encircles a portion of the second segment 200. The teeth/bumps circulate along an internal diameter and length of the switch 196. A person having ordinary skill in the art will readily understand that the set of grooves resembles the threading of a screw, while the set of teeth/bumps resembles the threading of a nut. The user/clinician pushes the switch 196 towards the proximal end 130 to activate the set of petals 194. Advancement of the switch 196 creates a frictional force by way of physical interaction between the grooves and teeth/bumps to prevent the switch 196 from sliding backwards (i.e. distally) to its original position. Alternatively, the second segment 200 can have a set of teeth/bumps and the switch 196 can have a corresponding set of grooves. In order to withdraw the sheath from the cannulated vessel, the user or clinician reverses the petal activation process by releasing the switch 196 away from the proximal end 130. The petals 194 thus retract, recede, or collapse into the space portions 195, allowing smooth withdrawal of the sheath from the vessel. A person having ordinary skill in the art can modify the switch 196 such that advancing the switch 196 proximally towards the proximal end 130 deactivates the petals 194, while retracting the switch 196 distally away from the proximal end 130 activates the petals 194.

In certain embodiments, such as that shown in FIG. 6A, a subset of petals 194 or each of the petals 194 is selectively activatable (e.g., petals 194 can be selectively activated on an individual basis, or in pairs). More particularly, each subset of petals 194 or each petal 194 is coupled to a switch 196 that facilitates or enables selective radial outward expansion of the subset of petals 194 or petal, respectively. The selective outward expansion can facilitate use of petals 194 of different sizes, and/or the activation of particular numbers of petals 194 depending upon the size of the cannulated vessel. In a further embodiment, the at least one switch 196 can include an activation port carried by a ring, which is configured to enable simultaneous outward expansion of the petals 194, emulating a single switch 196 that activates all the petals 194 simultaneously.

Figure 7:
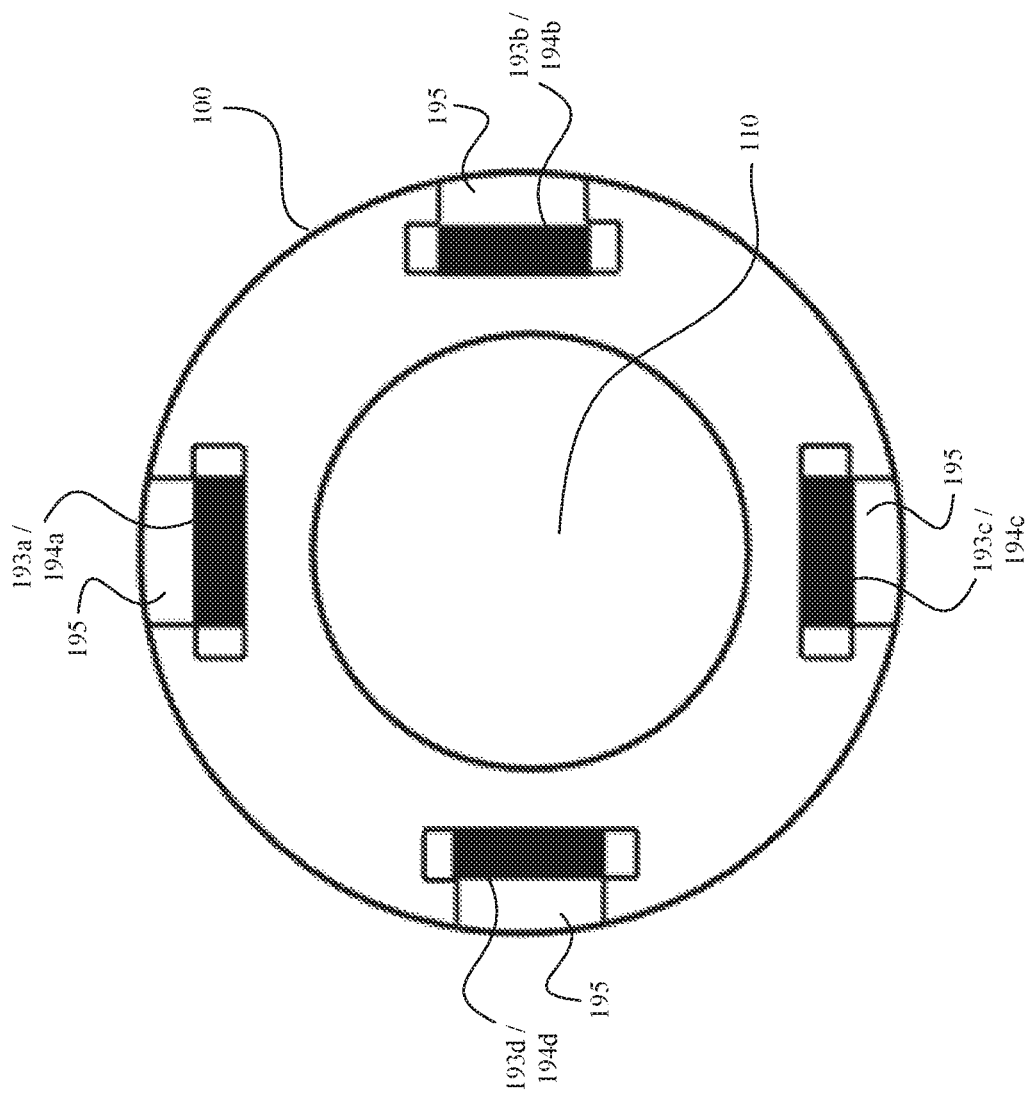
FIG. 7 is a schematic illustration of a cross section view of a representative arrangement of anchoring petals in accordance with an embodiment of the present disclosure.

FIG. 7 is a cross sectional illustration showing a plurality of strips 193 evenly distributed around the lengthwise/longitudinal/central axis of the first lumen 110. In a representative embodiment, the plurality of strips 193 includes four petals 194a-d. Alternatively, the anchoring assembly 190 may be suitably structured such that there are at least two strips 193 and hence at least two petals 194 that can act as anchoring points for anchoring the first segment 100 at an intended position within the cannulated vessel. In this embodiment, each of the strips 193/petals 194 is disposed 90° circumferentially apart from another strip 193/petal 194, and each of the strips 193 is housed within the space portion 195 as is each petal 194 when the petals 194 are inactivated or retracted (i.e., prior to or after the outward/radial expansion of the petals 194 beyond the outer circumference/diameter of the first segment 100).

One or more types of fluid impermeable barriers can reside within the space portions 195 in order to prevent the backflow of blood/fluid therethrough when the petals 194 are activated/deployed. For instance, one or more space portions 195 can include a compressible foam material (e.g., an open cell and/or closed cell foam) that extends along a predetermined short or generally short length of the space portion 195 (e.g., a few to several millimeters, or up to 1 centimeter), which fills those portions of the cross sectional area of the space portion 195 that are not occupied by a strip 193, and which provides a fluid impermeable barrier or seal between the inner walls of the space portion 195 and the outer periphery of the strip 193 disposed therein. Such a foam material can be disposed along one or more sections of a given space portion 195, such as slightly distal to the terminal end of the strip 193 that defines the petal 194 thereof, and/or slightly proximal to a switch displacement limit/stop structure. Alternatively or additionally, a strip 193 can carry a set of bumps, kinks, or ridges that occupy the internal cross-sectional area of its corresponding space portion 195, and which serve as fluid flow barriers within the space portion 195.

The petals 194 can be arranged relative to the portions of the length and a cross-sectional area/periphery/circumference of the first tube 10 in various manners, depending on embodiment details, such as in one or more manners analogous to those described above with respect to the fenestrations 140. Thus, depending upon an overall petal arrangement under consideration, some or all of the petals 194 can have an oblique arrangement or a non-oblique arrangement relative to a lengthwise/longitudinal/central axis of the first segment 100 or a fluid flow direction therein. For instance, in a non-oblique/perpendicular arrangement, a plane through a plurality or each of the petals 194 is perpendicular or essentially perpendicular to the axial direction of the first lumen 110, thereby forming an angle β of 90° with respect to the lengthwise/longitudinal/central axis of the first lumen 110. In contrast, in an oblique arrangement, a plane through a plurality of petals or each of the petals 194 forms a non-parallel and non-perpendicular angle β, i.e. an angle that is neither a right angle nor a multiple of a right angle, with respect to the lengthwise/longitudinal/central axis of the first lumen 110 or the direction of fluid flow therein. In some embodiments having an oblique petal arrangement, the angle β formed by the plane of the petals 194 is 45°. It will be apparent to a person having ordinary skill in the relevant art that other angles are possible, such as between 30° and 60°. It will be readily apparent to an individual having ordinary skill in the relevant art that the angle β in accordance with embodiments of this disclosure can be the same as or different than the aforementioned angle α in this disclosure. Thus, the petal orientation angle β can be different from or the same as the fenestration orientation angle α described above.

Referring again to FIG. 6B, compared to a non-oblique arrangement of petals 194, in an oblique petal arrangement the plane of the petals 194 is more parallel to the lengthwise/longitudinal/central axis of the cannulated vessel. An oblique petal arrangement can advantageously position the petals 194 more parallel or planar to the superficial wall of the cannulated vessel, which in turn can provide more effective abutment of the petals 194 on the superficial wall when the petals 194 are activated, thereby improving anchorage of the first segment 100 within the cannulated vessel. FIG. 6B illustrates an oblique arrangement of petals 194 in accordance with a representative embodiment of the present disclosure, in which the set of petals 194 includes a first petal 194a, a second petal 194b, a third petal 194c, and a fourth petal (where the fourth petal is not visibly shown). The petals 194 in this embodiment are distributed about the entire circumference of the first tube 10, distal to the set of fenestrations 140. In the case of four petals 194, the petals 194 can be positioned 90° circumferentially apart from each other. If there are three petals 194, they can be positioned 120° circumferentially apart from each other. The arrangement of the four petals 194a-d is oblique with respect to the axial direction of the first tube 10. In this representative embodiment, the first petal 194a is positioned closest to the distal end 230, the second petal 194b is positioned proximal to the first petal 194a, the third petal 194c is positioned proximal to the second petal 194b, and the fourth petal can be positioned at a counterpart location to the second petal 194b (i.e., the opposite side of the first tube 10). It will be apparent to a person having ordinary skill in the relevant art that other embodiments can utilize other numbers of petals 194, other angular separations between petals 194, and/or other distributions of petals 194 about the first tube's cross-sectional area/periphery/circumference (e.g., nonuniform distributions of petals 194, in which petals 194 are excluded from specific portions of the first tube's cross-sectional area/periphery/circumference, such as a lower or lower most portion/region thereof.

FIG. 8A to FIG. 8E are schematic isometric views of a sheath including an anchoring assembly 190 having at least one fluid (e.g., gas/air or liquid) pressurizable/expandable/inflatable anchoring element or structure in accordance with an embodiment of the present disclosure. In multiple embodiments, the pressurizable/expandable/inflatable anchoring element or structure includes a balloon or cuff 150 and/or flange-type or projection-type anchoring elements or structures 192 fluidically coupled thereto or carried thereby. When pressurized/expanded/inflated, the cuff 150 and/or anchoring elements 192 fluidically coupled thereto or carried thereby are configured to provide a cross sectional area that is larger than a cross sectional area of the first segment 100 at a location around the cross-sectional area, periphery, or circumference of the first segment 100 at which the expandable or inflatable cuff 150 and/or the anchoring elements 192 that are fluidically coupled thereto or carried thereby are disposed.

Figure 8A:
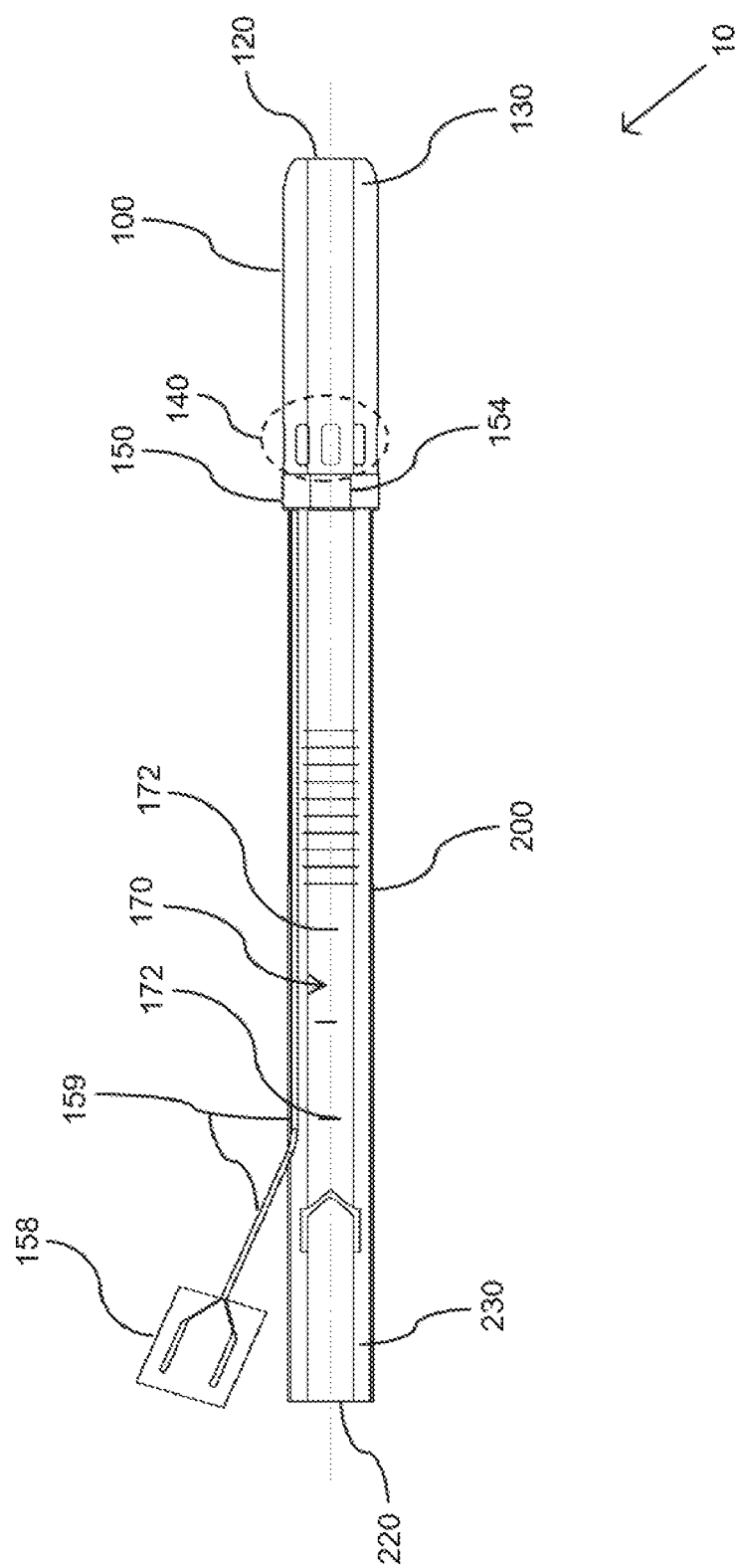
FIG. 8A to FIG. 8E are schematic illustrations of a sheath using an expandable/inflatable cuff in accordance with particular embodiments of the present disclosure.
Figure 8B:
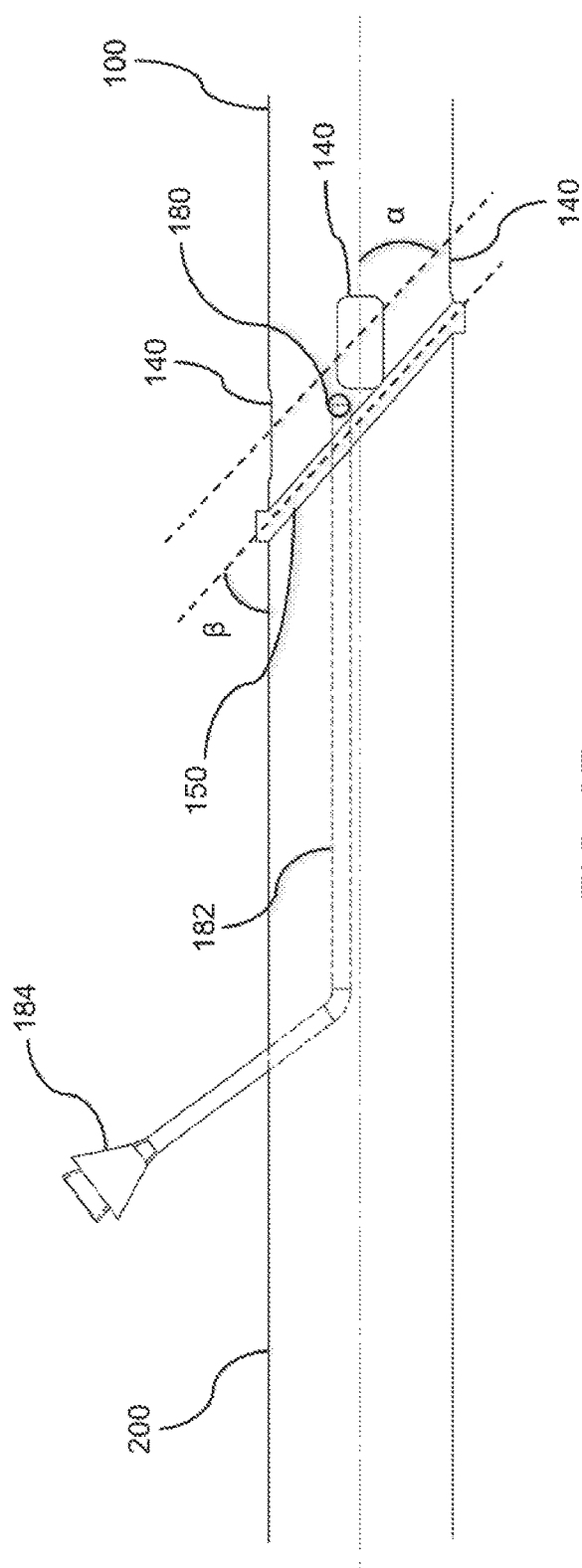
Figure 8C:
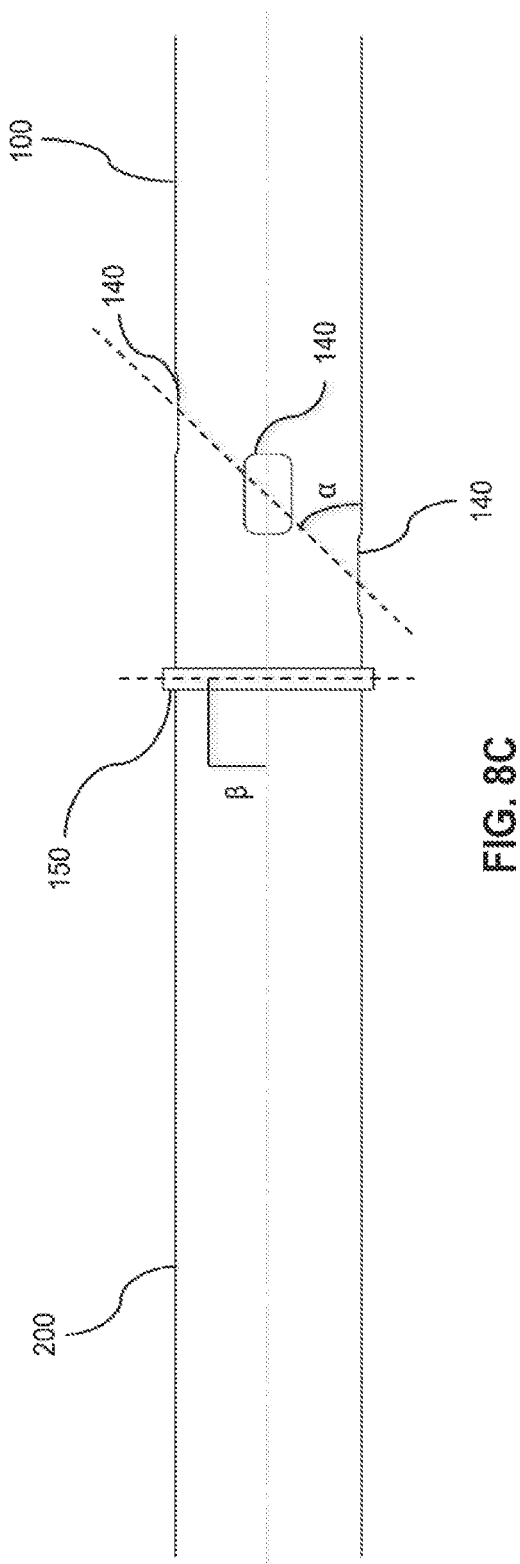
Figure 8D:
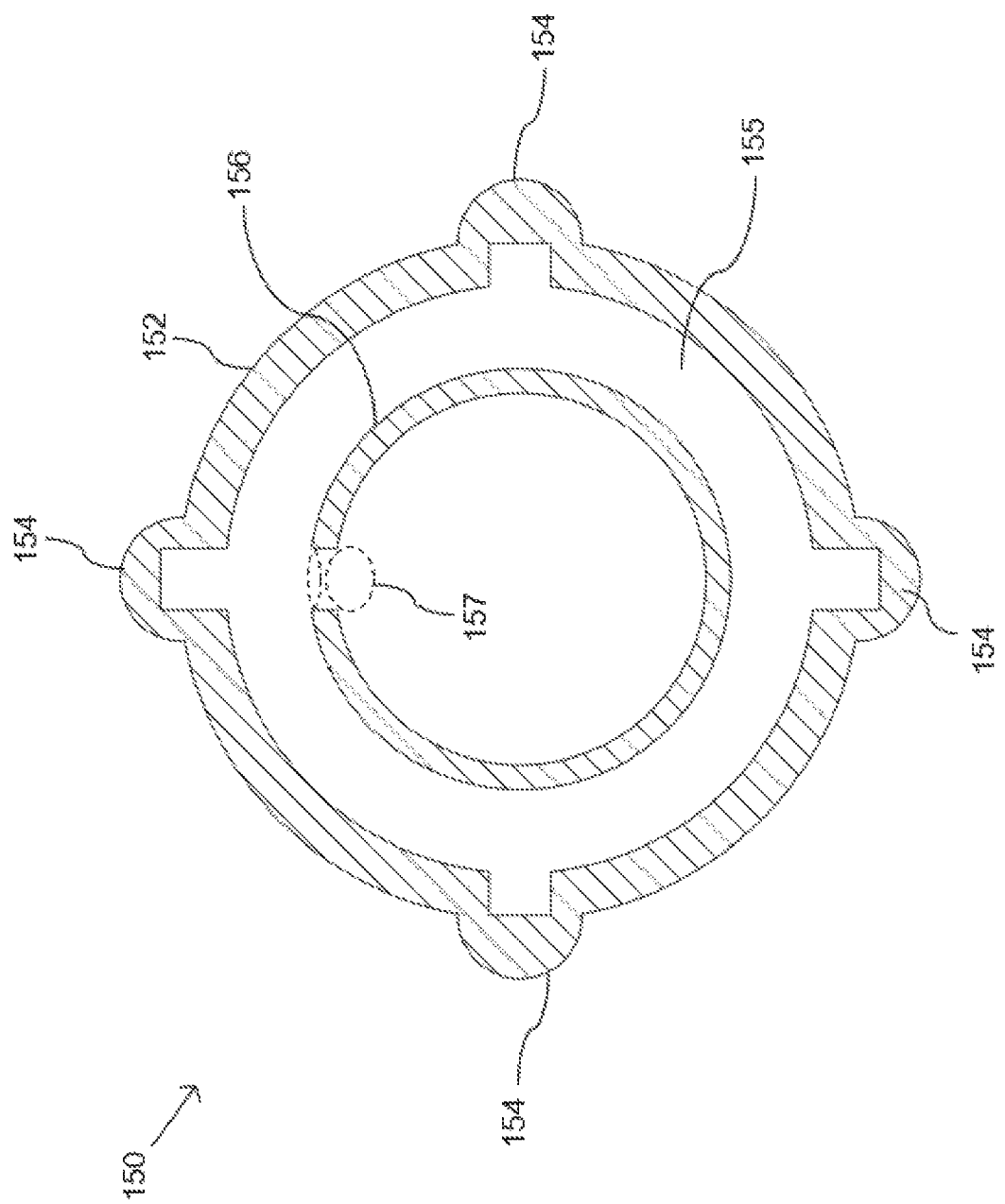

In multiple embodiments, the cuff 150 includes a pressurizable/expandable/inflatable elliptical or circular ring or annulus or semi-elliptical/semi-circular structure, segment, or partial annulus that is shaped and dimensioned to overlay or surround external, outer, or exterior portions of the first segment 100. Portions of the first tube 10 where the cuff 150 resides can have a reduced wall thickness compared to portions of the first tube 10 where the cuff 150 does not reside, such that when non-pressurized/unexpanded/deflated, the cuff 150 does not protrude or significantly protrude beyond the cross-sectional area/periphery/circumference of other portions of the first tube 10 at which the cuff 150 does not reside. Additionally, portions of the cuff 150 can be contoured/tapered/flanged or unflanged, or fluidically coupled to flange type elements. In particular, as shown in FIG. 8C, the cuff 150 can be fluidically coupled to and/or carry one or more flange(d) portions, elements, structures, or members 154 (e.g., a plurality of flange members 154) peripherally (e.g., circumferentially) disposed thereabout. The presence of flange members 154 can ensure that the cuff 150 allows blood/fluid flow around unflanged, recessed, or narrowed portions thereof, and hence a sheath that carries a cuff 150 in accordance with an embodiment of the present disclosure avoids impeding or completely impeding blood/fluid flow within the vessel especially when accidentally advanced further into the vessel (i.e., deeper than an intended or ideal position). The cuff 150 includes an outer/expandable layer 152; an inner layer 156; and a fluidically pressurizable compartment or chamber 155 therebetween. The cuff 150 includes an activation port 157 that is fluidically coupled to an inflation/deflation tube or pipe 159 that runs within or along portions of the inner wall of the sheath. The inflation/deflation tube 159 is further fluidically coupled to a one-way valve, valve portion, or valve assembly 158 (e.g., which includes at least one duck-bill or similar/analogous type of valve structure or valve). More particularly, the pipe 159 can be disposed within the thickness of the tube 10, or along a portion of an internal wall of the tube 10.

After the first tube's first segment 100 has been inserted into a vessel through an appropriate entry point, the cuff 150 can be expanded/inflated. Following such expansion or inflation, partial or slight withdrawal of the first tube 10 from the vessel causes portions of the cuff 150 and/or the flange members 154 fluidically coupled thereto and/or carried thereby to contact the vessel's superficial wall, which imparts a resistive force that impedes the partial withdrawal of the first tube 10, and which identifies to a clinician a position at which the fenestrations 140 are disposed near, very near, or just beyond the cannulation point, slightly or very slightly past the superficial vessel wall. The clinician can partially withdraw the first tube 10 slightly and gently until a resistive force that impedes the partial withdrawal of the first tube 10 is felt. Subsequent anchoring of the first tube's second segment 200 to the patient's skin allows two-point fixation (i.e., both internal and external to the patient) of the first tube 10 in an intended or correct position.

For pressurizing/expanding/inflating the cuff 150, air (or another gas or liquid) can be introduced by the user/clinician by applying a positive air pressure to the one-way valve assembly 158. As a result of pressurization/expansion/inflation of the cuff 150, the cuff 150 and/or flange members 154 fluidically coupled thereto/carried thereby expand outward/radially away from the first lumen 110, beyond the exterior surface of the first segment 100. As a result, portions of the cuff 150 and/or flange members 154 corresponding thereto, can abut or anchor to the inside surface or superficial wall of the cannulated vessel, thereby facilitating or enabling secure retention of the first segment 100 within the cannulated vessel at an intended position. After the completion of an endovascular surgery or transcatheter procedure, in order to retract the sheath the user/clinician can apply a sufficient negative pressure on the one-way valve assembly 158 so that the flanged cuff 150 depressurizes/contracts/deflates/collapses into a reduced or minimal volume or original shape. An individual having ordinary skill in the art will readily understand that in several embodiments, the one-way valve assembly 158 can be suctioned using a syringe to allow depressurization/contraction/deflation of the cuff 150 and the flange members 154 corresponding thereto or carried thereby. Consequently, the user/clinician is able to safely retract the sheath away from the superficial wall. In the event that there is a need for quicker release of air, it is possible that the clinician can forcefully cut or break the one-way valve assembly 158 and/or the attached tube 159.

Figure 8E:
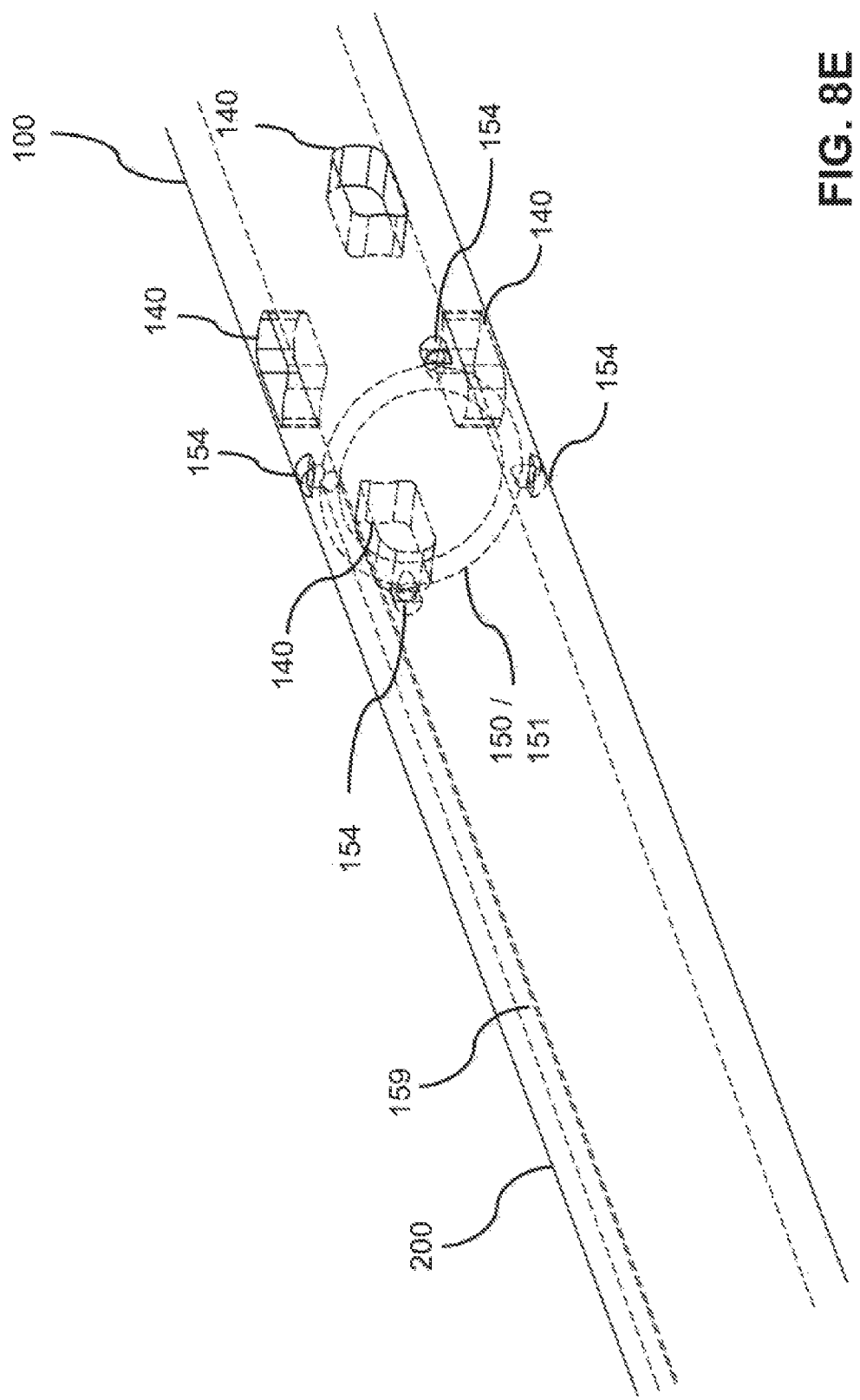

In specific embodiments, the cuff 150 can be carried internal to the first tube's outer or exterior surface, within portions of the first tube's wall; and first tube 10 can include apertures or windows through which a plurality of flange members 154 that are fluidically coupled to or carried by the cuff 150 can protrude beyond the exterior surface or outer diameter of the first segment 100 in response to pressurization/expansion/inflation of the cuff 150. Such an embodiment is illustrated in FIG. 8E. When the cuff 150 is depressurized/contracted/deflated, the flange members 154 can retract or recede back into the apertures or windows, such that the flange members 154 do not protrude or extend beyond the outer diameter or exterior surface of the first segment 100.

As an alternative to the foregoing, in some embodiments the pressurizable/expandable/inflatable cuff 150 can simply be replaced by annular/elliptical/circular fluid transport channel or fluid channel (e.g., an air transport channel or air channel) 151. The annular fluid channel 151 itself can be a rigid or generally rigid structure, rather than an expandable structure. In such embodiments, the annular fluid channel 151 resides internal to the outer/exterior surface of the first segment 100 of the first tube 10 (e.g., within internal portions of the wall thereof), and is fluidically coupled to a plurality of pressurizable/expandable/inflatable flange members 154 by way of a set of fluid communication port/passages, such that the flange members 154 are selectively outwardly/radially displaceable or inwardly displaceable as a result of the application of positive pressure or negative pressure to the annular air channel, respectively.

Depending upon embodiment details, flange members 154 can be pressurized/expanded/inflated collectively, such as in a uniform or generally uniform manner for multiple or all flange members simultaneously; or in a sequenced/sequential manner, depending upon how positive pressure is communicated thereto (e.g., some flange members 154 may more fully or fully pressurize/expand/inflate before other flange members 154).

Corresponding or analogous considerations apply to flange member depressurization/contraction/deflation as a result of the application of a negative pressure thereto.

Depending upon embodiment details, flange members 154 of the anchoring assembly 190 can be arranged non-obliquely or obliquely with respect to the axial or fluid flow direction of the first lumen 110, in a manner analogous to that described above for petals 194 and/or fenestrations 140. In a non-oblique arrangement, a plane through a plurality of flange members 154 is substantially perpendicular to the axial direction of the first lumen 110, such that the plane forms an angle β of 90° with respect to the axial direction of the first lumen 110. In an oblique arrangement, a plane through a plurality of flange members 154 forms a non-parallel and non-perpendicular angle β, i.e. an angle that is neither a right angle nor a multiple of a right angle, with respect to the axial direction of the first lumen 110.

Figure 9:
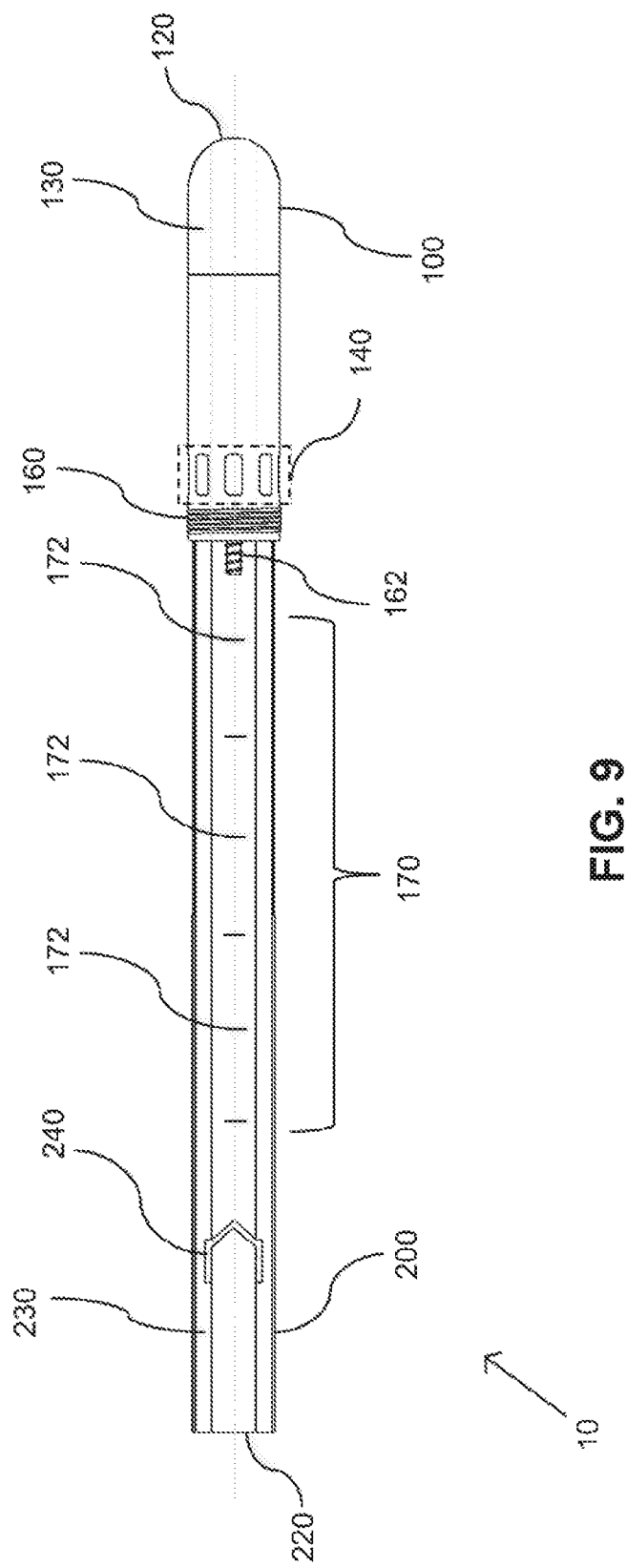
FIG. 9 is a schematic illustration of a sheath including a spring portion in accordance with an embodiment of the present disclosure.

FIG. 9 illustrates yet another embodiment of the anchoring assembly 190 in accordance with the present disclosure, in which the anchoring assembly 190 includes a spring portion 160 and an activation button 162 capable of activating the spring portion 160. In order to prevent accidental activation or springing of the spring portion 160, the anchoring assembly 190 further includes a catch portion adapted therefor, for selectively releasing or capturing the spring portion 160. The catch portion is positioned along the circumference of the first tube 10. Alternatively, the catch portion can be embodied within the sheath (internal to the wall of the sheath) but not along the internal diameter of the first tube 10. When in use, the user or clinician relies on the tension forces from the spring portion 160 to spring outwardly and laterally along the length of the first tube 10. The force within the spring portion 160 is designed to prevent displacement of the first tube 10, specifically the first segment 100, from the superficial vessel wall, thereby facilitating or enabling retention or anchoring of the first segment 100 within the cannulated vessel at an intended position.

In certain embodiments, the first tube 10 includes at least one graduated scale 170 disposed along the elongate length thereof. The graduated scale 170 can include at least one marking 172 along a portion of the length of the first tube 10, which is adapted to provide the user or clinician with a visual indication of a depth of entry into the vessel. By having a visual indication of the depth of entry, the clinician will have additional information of the depth of the sheath during cannulation. The marking(s) 172 can also indicate or facilitate the prevention of accidental displacement of the sheath once inserted.

In some embodiments of the present disclosure, the first tube 10 additionally or alternatively includes at least one other marking positioned along a surface of thereof. The at least one other marking is adapted to provide a visual indication of contortion of the first tube 10, i.e. whether the first tube 10 is positioned in an undesired manner or is twisted relative to a cannulated vessel. Each of the at least one other markings is correlated with or corresponds to the position of a fenestration 140 or a subset of fenestrations 140 in order to provide the user/clinician with a visual indication of the directions the fenestrations 140 are facing within the cannulated vessel. Such markings can thus be positioned at an angular separation from each other that corresponds to the angular separation of fenestrations 140. In certain embodiments, the at least one other marking include a first mark site and a second mark site, wherein the alignment or positioning together of both mark sites indicates that the first tube 10 is substantially straight or is formed in a straight manner. The use of such markings mitigates the risk of accidental contortion or twist of the first tube 10, or any part of the sheath, while in use. The sheath is thus adapted to provide a quick and effective visual indication of an angle of twist of the first tube 10 while the first tube 10 is inside the cannulated vessel.

Referring again to FIG. 5, a representative illustration is shown of portions of the sheath's first and second segments 100, 200 positioned relative to a vessel entry site or point 8 by which the first segment 100 of the first tube 10 has been positioned within a vessel 2. The vessel 2 includes a superficial wall 4 and a deep vessel wall 6, in a manner readily understood by one having ordinary skill in the relevant art. As indicated in FIG. 5, in various embodiments the fenestrations 140 are disposed on a flexible or semi-flexible angulatable section, element, member, or material 112 that is connected to or formed within the first segment 100. Once the fenestrations 140 have entered into the vessel 2, a portion of the first segment 100 distally adjacent or very near to the anchoring members 192 can resemble a curve or an elbow by way of bending provided by the angulatable section 112. The bending causes the first tube 10 to displace or angulate into a second position. The angulatable section 112 can establish an intended or predetermined angular orientation or angle between the first and second segments 100, 200, for instance, approximately 450. Notwithstanding, the angulatable section's range of angulation can be from 00 to 180°, or a fraction thereof. The anchoring members 192 are disposed on the first segment 100, slightly distal to the angulatable section 112. The majority of the length of the first segment 100 extends into the vessel 2, such that the proximal opening 120 resides at an intended or predetermined vascular location or target site. In some embodiments, the angulatable section 112 can be structurally reinforced to enhance structural reliability, for instance, by way of one or more of material composition selection, material thickness selection, and/or the incorporation of one or more types of fibrous strands or materials (e.g., biocompatible natural or synthetic bendable fibers such as carbon fibers, optical fibers, or silk fibers), which can be oriented along predetermined directions, such as lengthwise/cross-wise/spiral-wise, relative to the elongate length of the first tube's first segment 100) in and/or through one or more portions of the angulatable section 112. As blood/fluid enters into the first tube 10 by way of the proximal opening 120, a first portion of the blood that has entered the proximal opening 120 distally flows within the first lumen 110 in a first direction D1, and a second portion of the blood exits the fenestrations 140 in a set of distal flow directions D2.

A person having ordinary skill in the art will readily understand that the angulation of the first tube 10 is not necessarily or required, depending upon the manner in which the first tube is used. Alternatively, a non-angulatable first tube 10 can be regarded as being angulated at 0° to 180°, as described above in the range of angles.

In multiple embodiments, the sheath includes an indication display unit connected to a blood pressure flow meter adapted to provide information to the clinician to ensure the blood is flowing in a desired manner. Alternatively or additionally, the first tube 10 includes a blood/fluid indicator port 180 positioned between the resistance portion 197 and the fenestrations 140, such as shown in FIG. 8B. For instance, the blood/fluid indicator port 180 is positioned at a predefined distance distally away from the proximal end 130 of the first tube 10, and adjacent to or near the set of fenestrations 140, but in several embodiments not proximally beyond the positions of the fenestrations 140.

The blood/fluid indicator port 180 is fluidically coupled to a fluidic passage or channel channel 182, portions of which extend a predetermined length internal to the wall of the first segment 100 of the tube 10, and/or along the exterior surface of the first tube 10 depending on embodiment details. The channel 182 is further fluidically coupled to a blood/fluid indicator interface 184, which can provide an indication (e.g., a visual and/or auditory indication) of the presence of blood thereat. The blood/fluid indicator port 180 and the channel 182 fluidically coupled thereto are adapted to allow backward, i.e. distal, flow of blood, as well as for retrieval or withdrawal of blood samples or specimens for testing if needed. In addition, contrast agents can be injected into the vessel through blood/fluid indicator port 180 via the fluid indicator interface 184 or the channel 182 in the opposite direction to perform contrast study or angiogram of the above vessel.

The channel 182 can be fluidically coupled to a manometer for measurement of intra-arterial blood pressure, or to a pressure transducer device to measure vascular pressure, thereby ensuring that the sheath is inserted into the correct vessel. A person having ordinary skill in the art will readily understand that blood/fluid flowing backward along the channel 182 can be directed to any suitable blood pressure measuring apparatus for providing the clinician with knowledge of systolic and diastolic blood pressures.

In various embodiments, the channel 182 is formed of a suitable transparent or translucent material, such that the presence of blood therein can be readily visually observed by the clinician. The fluid indicator interface 184 and/or the channel 182 can thus provide a visual indication to a clinician of the internal flow of blood/fluid within the channel 182, and also whether the anchoring elements and the fenestrations 140 have entered the cannulated vessel 2. More particularly, in several embodiments, the blood/fluid indicator port 180 once inside the cannulated vessel allows backflow of blood/fluid into and along the channel 182 to provide the clinician with a visual indication that the fenestrations 140 and the anchoring elements of the anchoring assembly 190 are in position within the vessel lumen, indicating that the clinician may effectuate, deploy, or activate the anchor assembly 190 safely.

Once the clinician obtains a visual indication that the fenestrations 140 are within the diameter of the vessel or artery, the clinician can then advance the sheath a short distance further (e.g., about or at least 1 centimeter), and activate the anchoring assembly 190. The first tube 10 is then pulled back until some resistance is felt. This resistance is due to the anchoring members 192 (e.g. petals 194 or flange members 154) coming into contact with or abutting the superficial vessel wall 4. The sheath is then anchored to the skin at this point, providing at least a two-point fixation for securing, retaining, or maintaining the first tube 10 in an intended position. The clinician can then insert and subsequently deploy or activate or effectuate another device, such as a self-expandable stent graft or transcatheter device, through the first tube 10 of the sheath.

In some embodiments, the fluid indicator assembly can include a luminous portion, which when contacted with blood/fluid enhances the brightness thereof to create an enhanced visual indication or direct attention to fluid flow along portions of the channel 182, in a direction away from the blood/fluid indicator port 180. The luminous portion carries therein a relatively small amount of a substance that when reacted with blood/fluid causes the blood/fluid to visually appear brighter. Such a substance can include a garnet or borate single crystal containing thorium (Th) or a liquid crystal material. The luminous portion can be disposed in a variety of positions along the length of the channel 182. For example, the luminous portion can be positioned adjacent to the blood/fluid indicator port 180 so that the enhanced brightness effect provided thereby upon the blood/fluid appears visually more obvious essentially immediately after the blood/fluid has entered the blood/fluid indicator port 180. Due to differential pressure, the blood/fluid within the cannulated vessel 2 flows into the blood/fluid indicator port 180 and interacts with the luminous portion, thereby visually enhancing the brightness of the blood/fluid.

The visually enhanced portion of the blood/fluid is gradually pushed along the length of the channel 182 in a distal direction towards the fluid indicator interface 184.

An individual having ordinary skill in the relevant art will recognize that sheath assemblies, structures, and portions thereof in accordance with embodiments of the present disclosure can exhibit dimensions which are appropriate for the type of patient or subject (e.g., an infant or child versus a full grown adult) and/or the nature of a clinical situation under consideration. Depending upon embodiment or situational details, the first tube 10 can typically (but not exclusively) have an outer diameter of Gauge 10 (in children) to Gauge 21 (in adults) on the French Catheter Scale, depending upon the age and/or size of patient under consideration.

There is a tendency for the sheath to bend out of shape prior to use. This is because of the relatively long length of the sheath. A person skilled in the art will readily understand that the wavering of the sheath relates to kinking. In order to address the problem, at least one steel, plastic, or other metal wire reinforcement portion is suitably positioned along the internal diameter and length of the first tube 10. Each of the reinforcement portions is suitably positioned along at least some length of the first tube 10. The reinforcement portions may also be suitably embodied by any suitable material such as plastics, clear PVC, polyurethane, polyvinyl, or any other suitable material that are commercially available.

A sheath is described in accordance with an embodiment of the present disclosure, wherein the first tube 10 is inserted into an artery (e.g., the right femoral artery) of a body extremity (e.g., the right leg, correspondingly). Blood that is supplied to the first tube's proximal opening 120 can flow into the lumen of the first tube 10, and simultaneously blood can flow out of the first tube's fenestrations 140 away from the heart and into the cannulated extremity. Thus, blood pumped from the heart or a pumping source/blood flow source is channeled along the first tube 10 and towards, to, and out of the fenestrations 140 in order to prevent limb, head, or other distal ischemia. A person skilled in the art will readily understand that the pumping/blood flow source can be the heart or other suitable means capable of pumping blood (e.g., an artificial or mechanical pumping device internal or external to the body, such as a replacement heart, artificial heart, ventricular assist device, etc.).

The first tube 10 includes a set of one one-way valve assemblies or one-way valves 240 positioned at or near the distal end 230. The first tube 10 can also include more than a single one-way valve 240 (e.g., the first tube 10 can include or be fluidically coupled to two or more one-way valves 240). Thus, the sheath, when used in an endovascular or transcatheter procedure setting, prevents blood/fluid (e.g., a first portion of the blood/fluid that entered the proximal opening 120) from flowing beyond the one-way valve(s) 240, i.e., backflow is avoided, while at the same time allowing vascular access in the proximal direction. Backflow of blood/fluid can be defined as distal flow of blood/fluid beyond the one-way valve 240, out of the sheath. The sheath is thus used as a passive conduit for both vascular access and distal perfusion, in a manner understood by an individual having ordinary skill in the relevant art.

Figure 10:
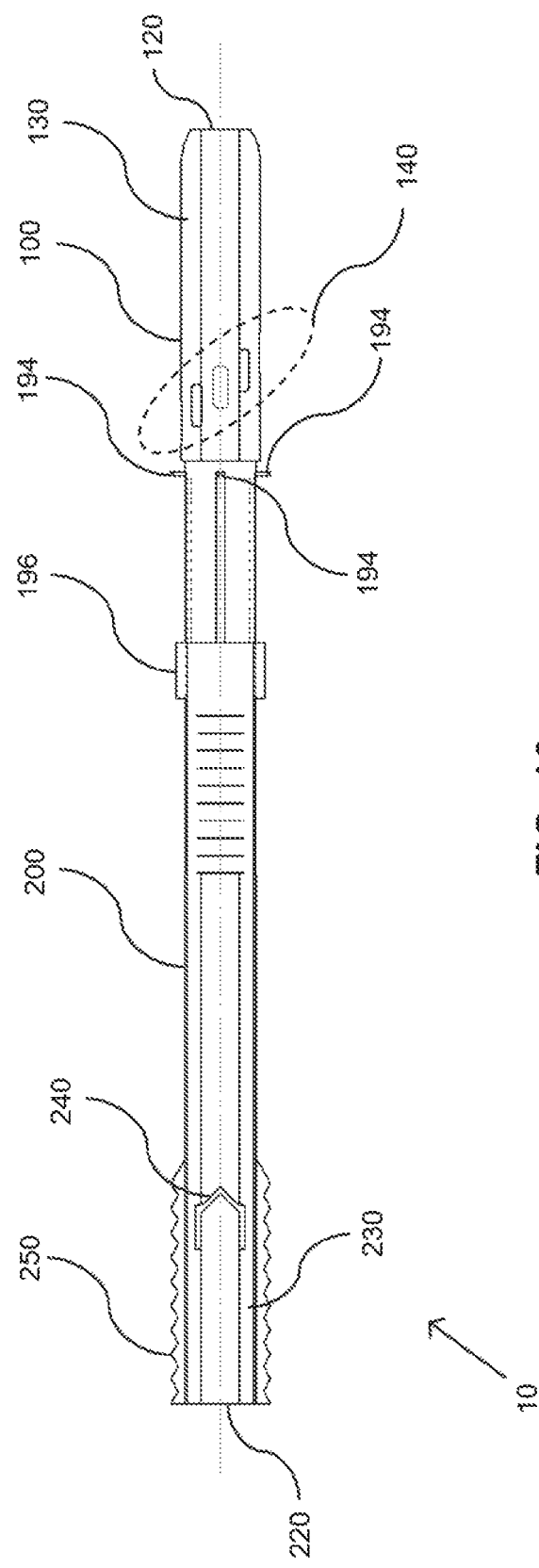
FIG. 10 is a schematic illustration of a sheath having a screwable portion in accordance with an embodiment of the present disclosure.

Each one-way valve 240, when used in the context of the endovascular surgery or transcatheter procedure, acts as a closed or closeable tap. The one-way valve 240 is adapted to expand and adapt to the size and shape of a second elongated through tube 20, such as for a dilator, self-expandable stent graft, or transcatheter device. Referring to FIG. 10, the first tube 10 can further include a screwable portion 250 positioned close to its distal end 230. The screwable portion 250 is meant to provide the user or clinician with an alternative manner of securing the first tube 10, and thus the sheath, such that minimal movement occurs during an operation or procedure. This screwable portion may also reside within or facing towards/into the lumen 210. A person having ordinary skill in the art will appreciate that blood/fluid will not flow across the one-way valve(s) 240 at the distal end 230 of the sheath, thereby maintaining a constant blood/fluid pressure during the operation or procedure.

The second tube 20 is known to individuals having ordinary skill in the art as a dilator to stiffen the first tube 10 for vessel entry. Upon successful entry into the vessel and suitable fixation as described above, the dilator may be withdrawn, and at least one self-expandable stent graft or transcatheter device can be advanced towards and across the first tube 10 into the aorta and/or heart. The clinician can deploy the at least one self-expandable stent graft or transcatheter device as required and still maintain blood/fluid flow along an artery when a portion of the first tube 10 is within the artery. A sheath or vascular sheath in accordance with an embodiment of the present disclosure is thus useful in multi-step procedures where more than one endovascular or transcatheter device is deployed, especially when instrumentation using smaller caliber devices—e.g. catheters, guide catheters, and/or guide wires—is required in between deployment of larger caliber transcatheter devices. The sheath allows distal perfusion in between deployment of stent grafts/transcatheter devices, and at the same time maintains adequate vascular access. The sheath can also be used in complex endovascular/transcatheter procedures requiring simultaneous access for multiple smaller sheaths or catheters, guide catheters, guide wires and/or devices while at the same time maintaining distal perfusion. Such multiple catheters, guide wires and/or devices can be used and/or deployed simultaneously by "double-puncture", "triple-puncture", or "quadruple-puncture" of the leaflets of the one-way valve(s) 240 of the sheath to allow access to the vasculature/heart.

For instance, in association with an endovascular procedure that employs the first tube 10 in accordance with an embodiment of the present disclosure, the first tube 10 can be inserted into an artery (e.g. the right femoral artery) or a body extremity (e.g. the right leg, correspondingly). Blood entering the proximal opening 120 of the first tube 10 is channeled along the first tube's lumen. In other words, the blood is able to flow into the first lumen 110 and the second lumen 210. Additionally, blood can simultaneously distally flow out the fenestrations 140 and into the limb, head, or other distal region. When the sheath is in use (i.e. when the vessel is cannulated/inserted) into a patient or subject such that blood or fluid or fluid with dye can flow from the proximal opening 120 of the first tube 10, such blood or fluid is channeled towards the fenestrations 140. A first portion of the blood or fluid or fluid with dye flows into the lumen of the first tube 10, while a second portion of the blood or fluid further exits the fenestrations 140 into the vessel. Specifically, the second portion of the blood flows beyond the confinement of the lumen of the first tube 10 into the vessel, such that the second portion of the blood is channeled to the limb, head, or other distal region.

Figure 11:
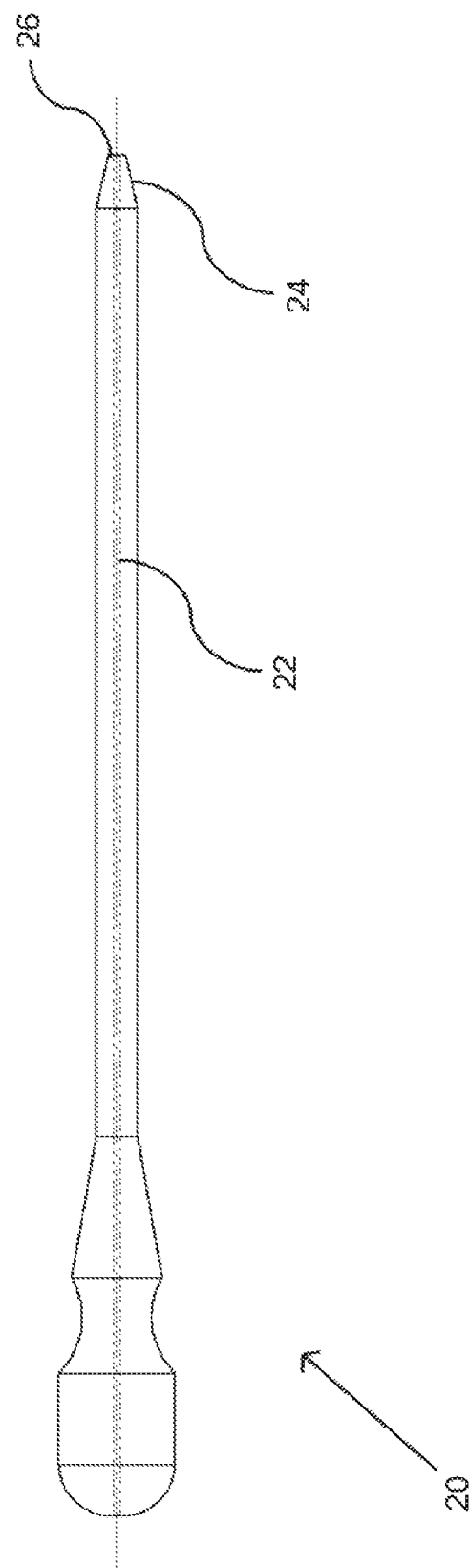
FIG. 11 is a schematic illustration of a second tube provided by a sheath assembly or structure in accordance with an embodiment of the present disclosure.

FIG. 11 is a schematic illustration of a second tube 20 provided by a sheath assembly in accordance with an embodiment of the present disclosure. An individual having ordinary skill in the relevant art will readily understand that the second tube 20 corresponds to or is a dilator assembly or dilator 20. Thus, the dilator 20 can be inserted into the lumen of the first tube 10. The diameter of the dilator 20 corresponds to the internal diameter of the first tube 10. More particularly, the second tube 20 has a diameter smaller than the first tube 10, and is engageable therewith. The dilator 20 includes an inner lumen or a central guide wire channel 22 configured for engaging with or passing a guide wire, as well as a tapered distal end 24 having a diameter that occludes the proximal opening 120 of the first tube 10. The tapered distal end 24 includes a through hole or opening therein 26 configured for passage of the guide wire. The guide wire can be 0.014 inch or 0.018 inch or 0.035 inch in diameter. The dilator 20 can include a frictional portion positioned at one end adapted to provide grip while in use. In use, the guide wire directs entry of the dilator 20 (together with the sheath) into the vessel 2. Thus, the dilator 20 or second tube 20 facilitates or enables percutaneous insertion of the first tube 10 into the vessel 2. The dilator 20 supports, straightens, and stiffens the first tube 10, thereby smoothening entry as the first tube 10 is inserted into the vessel 2. Further, the dilator 20 can be lubricated with a suitable material such that the insertion of the dilator 20 into the first tube 10 becomes smoother.

Figure 12A:
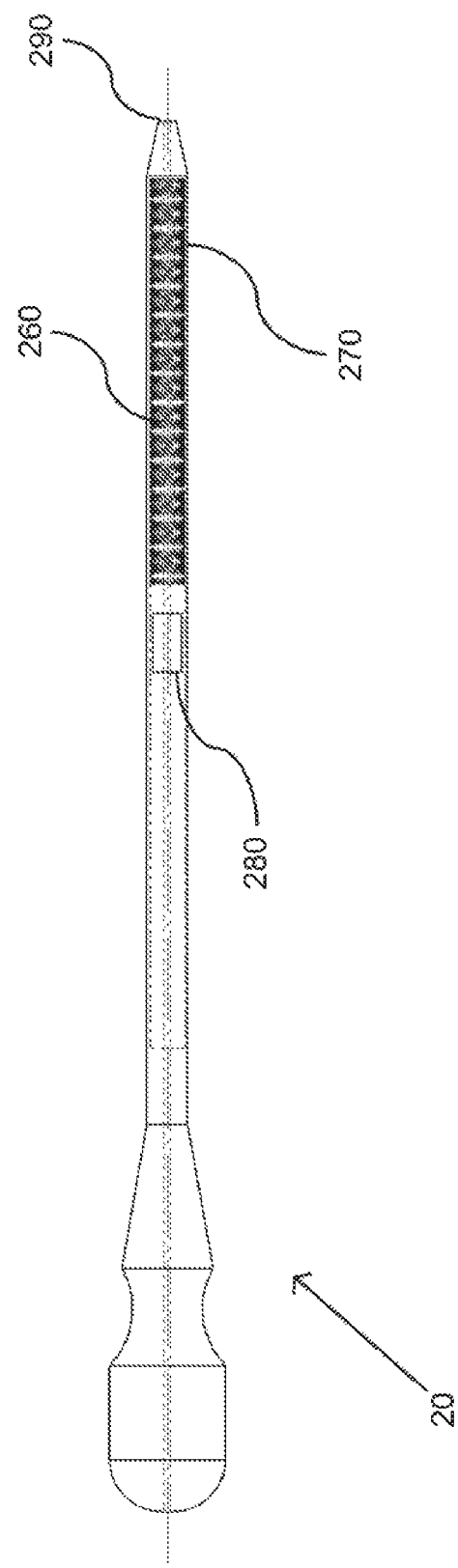
FIGS. 12A and 12B are schematic illustrations of a second tube including a self-expandable stent graft in accordance with an embodiment of the present disclosure.
Figure 12B:
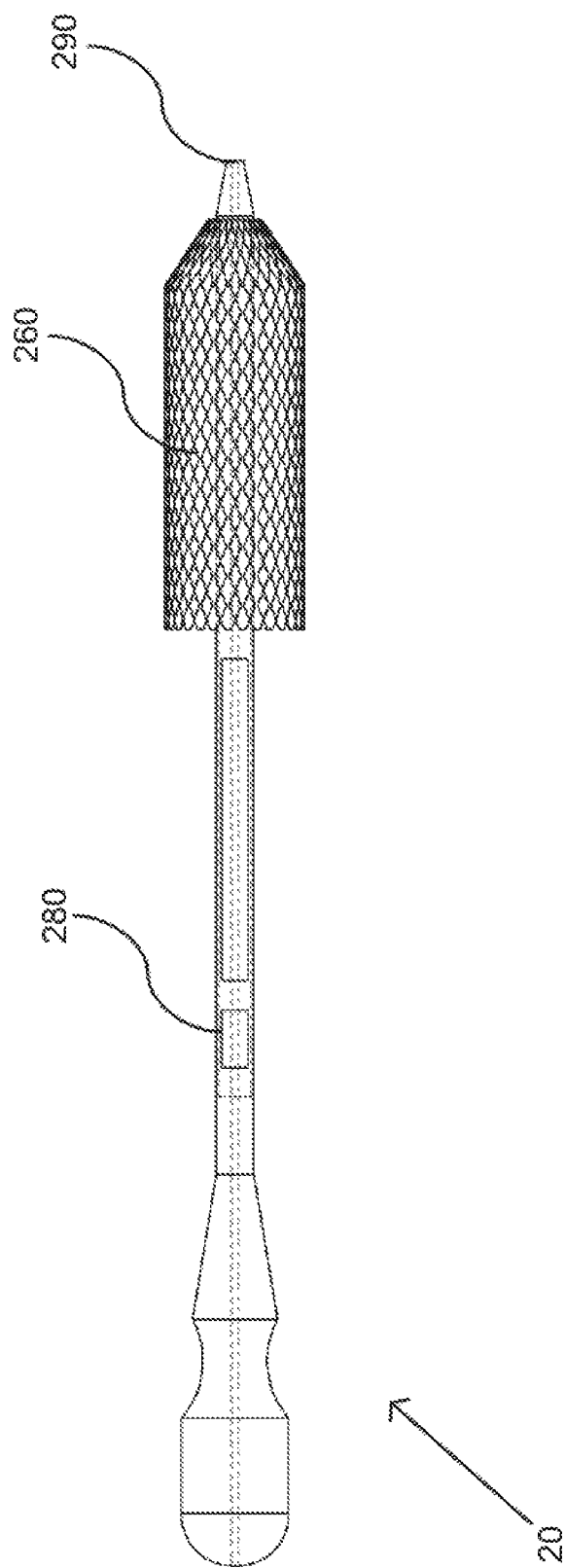

FIG. 12A and FIG. 12B are schematic alternative illustrations of a second tube 20 provided by a sheath assembly in accordance with an embodiment of the present disclosure. In a secondary use, a self-expandable stent graft 260 is embodied or encased within a portion of the second tube 20 while being mounted on an inner dilator. The second tube 20 has a slideable casement 270 configured to cover and prevent the stent graft 260 from expanding. The slideable casement 270 may be connected and linked to a slideable button 280 for uncovering the self-expandable stent graft when the slideable casement 270 is moved from a first slideable position to a second slideable position.

When the second tube 20 is in the first slideable position, the stent graft 260 is in an unexpanded state. When the second tube 20 is in the second slideable position, the stent graft 260 is in an expanded state. The user/clinician holds and retracts the slideable button 280 to allow the stent graft 260 to expand. The second tube 20 has a diameter smaller than the first tube 10, and is engageable therewith. The second tube 20 is used with a guide wire as described above. A person having ordinary skill in the art will readily understand that the stent graft 260 should be suitably positioned closer to the proximal end 290 of the second tube 20. In addition, the diameter of the second tube 20 should preferably be uniform or constant.

Aspects of particular embodiments of the present disclosure address at least one aspect, problem, limitation, and/or disadvantage associated with existing sheaths, sheath assemblies, sheath devices, or sheath structures. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

The invention claimed is:

1. A sheath structure configured for cannulating an anatomical vessel by way of entry into the vessel at a cannulation site, the sheath structure having a diameter and comprising:
a first tube having a central axis extending in an axial direction along an elongate length of the first tube, a distal end, a proximal end, and a lumen therebetween for channeling a fluid, the first tube including:
  a distal portion coupled to the distal end and configured for receiving an endovascular or transcatheter device;
  a valve portion disposed near or at the distal end, the valve portion including at least one valve and having a plurality of leaflets configured as a closed tap to prevent backflow of a first portion of the fluid out of the distal end, the valve portion configured to expand and adapt to the size and shape of a device having a smaller diameter than the sheath structure including one of a dilator, a self-expandable stent graft, a sheath, a catheter, and a transcatheter device, and the valve portion configured to accept multiple smaller diameter devices for a double puncture, a triple puncture, or a quadruple puncture procedure; and
a first segment introducible into the vessel and configured to entirely reside within the vessel when the vessel is cannulated, the first segment having: a wall, a flexible or semi-flexible angulatable section, and a lengthwise axis, the first segment comprising:
  a first lumen therein fluidically coupled to the lumen of the first tube, and which extends along the lengthwise axis;
  a proximal opening configured for receiving the fluid by way of a pumping source and channeling the fluid into the first lumen;
  a set of fenestrations disposed distal to the proximal opening and fluidically coupled thereto, the set of fenestrations carried by the angulatable section and configured for distally outputting or discharging a second portion of the fluid into the vessel; and
  a radially or outwardly displaceable anchoring assembly carried by the first segment near or adjacent and distal to the set of fenestrations, wherein the anchoring assembly comprises:
    a first radially or outwardly displaceable portion and a second radially or outwardly displaceable portion, which are spaced circumferentially apart from each other around the first segment; and
    a set of activation elements configured to radially or outwardly displace the first radially or outwardly displaceable portion and the second radially or outwardly displaceable portion in response to clinician activation of the set of activation elements,
    wherein the first radially or outwardly displaceable portion and the second radially or outwardly displaceable portion are:
      (a) each configured to abut the superficial wall of the vessel at the cannulation site as well as provide resistance to clinician pull back of the first tube by abutting the superficial wall of the vessel (i) after entry of the first segment into the vessel at the cannulation site including entry of the set of fenestrations, the first radially or outwardly displaceable portion, and the second radially or outwardly displaceable portion into the diameter of the vessel, followed by (ii) clinician activation of the set of activation elements; and
      (b) arranged obliquely with respect to each other relative to the central axis extending in the axial direction along the elongate length of the first tube prior to as well as after clinician activation of the set of activation elements.

2. The sheath structure of claim 1, wherein the set of fenestrations is configured for outputting or discharging a second portion of the fluid into the vessel in at least one distal flow direction, wherein the at least one distal flow direction has a distal vector flow component parallel to the lengthwise axis of the first segment.

3. The sheath structure of claim 1, wherein the set of fenestrations is disposed on at most a lower portion or a lower half of the periphery of the first segment that is intended to face away from a superficial wall of the vessel.

4. The sheath structure of claim 1, wherein:
the first tube further comprises a second segment comprising a second lumen aligned with the first lumen, wherein the second segment is distal to the first segment, and wherein the second segment is configured to substantially entirely reside external to the vessel when the vessel is cannulated;
the angulatable portion is configured to bend to form a curve or elbow between the first segment and the second segment; and
prior to angulatable section bending and prior to radial or outward displacement of the first radially or outwardly displaceable portion and the second radially or outwardly displaceable portion: the first radially or outwardly displaceable portion is disposed closest to the proximal end of the first tube at a first circumferential position about the first segment, and the second radially or outwardly displaceable portion is disposed distal to the first radially or outwardly displaceable portion at a second circumferential position about the circumference of the first segment distinct from the first circumferential position.

5. The sheath structure of claim 1, wherein the set of fenestrations comprises a first fenestration and a second fenestration disposed at different distal locations relative to each other along the first segment and different circumferential locations relative to each other along the first segment, and wherein the first radially or outwardly displaceable portion is disposed distal to the first fenestration, and the second radially or outwardly displaceable portion is disposed distal to the first radially or outwardly displaceable portion, the first fenestration, and the second fenestration.

6. The sheath structure of claim 1, wherein the first tube further comprises a second segment comprising a second lumen aligned with the first lumen, wherein the second segment is distal to the first segment, wherein the second segment is configured to substantially entirely reside external to the vessel when the vessel is cannulated, wherein the first and second lumens form the lumen of the first tube, and wherein the valve portion comprises a set of one-way valves disposed in the second segment.

7. The sheath structure of claim 1, wherein the anchoring assembly comprises one of:

(a) a first pressurizable/depressurizable cuff carried by external portions of the first segment, and an inflation tube coupled to a one-way valve assembly configured for first pressurizable/depressurizable cuff inflation by way of clinician application of a positive air or fluid pressure thereto; and (b) a second pressurizable/depressurizable cuff or an annular air or fluid channel carried internal to an external surface of the first segment within portions of the wall of the first segment, and a plurality of anchor members fluidically coupled to or carried by the second pressurizable/depressurizable cuff or the annular air or fluid channel, wherein the plurality of anchor members is configured to radially expand/contract relative to the lengthwise axis of the first segment in response to pressurization/depressurization of the second pressurizable/depressurizable cuff or the annular air or fluid channel, such that the plurality of anchor members can selectively protrude beyond or through the wall of the first segment in directions away from the lengthwise axis of the first segment.

8. The sheath structure of claim 7, wherein portions of the wall of the first segment at which the first pressurizable/depressurizable cuff reside have a reduced wall thickness compared to other portions of the first segment where the first pressurizable/depressurizable cuff does not reside.

9. The sheath structure of claim 1, wherein the pumping source is an artificial or mechanical pumping device capable of transferring blood within the vessel.

10. The sheath structure of claim 1, wherein the sheath structure is configured to maintain distal perfusion during an endovascular or transcatheter procedure.

11. The sheath structure of claim 1, further comprising a fluid indicator port disposed on the first segment, which is coupled to a translucent or transparent fluidic channel configured for providing a visual indication of the presence of fluid into the fluid indicator port.

12. A sheath structure configured for cannulating an anatomical vessel, the sheath structure comprising:

a first tube having an elongate length, a distal end, a proximal end, and a lumen therebetween for channeling a fluid, the first tube including:

a distal portion coupled to the distal end and configured for receiving an endovascular or transcatheter device;

a valve portion disposed near or at the distal end, the valve portion including at least one valve and having a plurality of leaflets configured as a closed tap to prevent backflow of a first portion of the fluid out of the distal end, the valve portion configured to expand and adapt to the size and shape of a device having a smaller diameter than the sheath structure including one of a dilator, a self-expandable stent graft, a sheath, a catheter, and a transcatheter device, and the valve portion configured to accept multiple smaller diameter devices for a double puncture, a triple puncture, or a quadruple puncture procedure; and a first segment configured to entirely reside within the vessel when the vessel is cannulated, the first segment comprising:

a first lumen therein fluidically coupled to the lumen of the first tube;

a proximal opening configured for receiving the fluid by way of a pumping source and channeling the fluid into the first lumen; and a set of fenestrations disposed distal to the proximal opening and fluidically coupled thereto, the set of fenestrations configured for distally outputting or discharging a second portion of the fluid into the vessel, and a fluid indicator port disposed on the first segment, which is coupled to a translucent or transparent fluidic channel configured for providing a visual indication of the presence of fluid into the fluid indicator port, wherein the channel includes a luminous portion that carries therein a substance which when reacted with blood/fluid causes the blood/fluid to visually appear brighter.

* * * * *